(12) United States Patent
Flochlay-Sigognault et al.

(10) Patent No.: US 11,878,006 B2
(45) Date of Patent: *Jan. 23, 2024

(54) ISOXAZOLINE SOLUTION CONTAINING VITAMIN E FOR USE WITH SANITIZED DRINKING WATER

(71) Applicant: Intervet Inc., Madison, NJ (US)

(72) Inventors: Annie Flochlay-Sigognault, Angers (FR); Anne Lehay, Angers (FR)

(73) Assignee: Intervet Inc., Rahway, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/390,258

(22) Filed: Jul. 30, 2021

(65) Prior Publication Data

US 2021/0354283 A1 Nov. 18, 2021

Related U.S. Application Data

(63) Continuation of application No. 16/253,780, filed on Jan. 22, 2019, now Pat. No. 10,569,410, which is a continuation of application No. 15/735,252, filed as application No. PCT/EP2016/064449 on Jun. 22, 2016, now abandoned.

(30) Foreign Application Priority Data

Jun. 23, 2015 (EP) ..................... 15173454

(51) Int. Cl.
| | | |
|---|---|---|
| A61K 31/42 | (2006.01) | |
| A61P 33/00 | (2006.01) | |
| A61K 31/355 | (2006.01) | |
| A61K 31/422 | (2006.01) | |
| A61K 47/22 | (2006.01) | |

(52) U.S. Cl.
CPC ............ *A61K 31/42* (2013.01); *A61K 31/355* (2013.01); *A61K 31/422* (2013.01); *A61K 47/22* (2013.01); *A61P 33/00* (2018.01)

(58) Field of Classification Search
CPC .... A61K 31/42; A61K 31/355; A61K 31/422; A61K 47/22; A61P 33/00
See application file for complete search history.

(56) References Cited

U.S. PATENT DOCUMENTS

| | | | | |
|---|---|---|---|---|
| 8,563,474 | B2* | 10/2013 | Koerber | A61K 31/277 |
| | | | | 548/240 |
| 2005/0005868 | A1* | 1/2005 | Shepard | C02F 1/76 |
| | | | | 119/72 |
| 2012/0309620 | A1 | 12/2012 | Koerber et al. | |
| 2013/0065846 | A1 | 3/2013 | Soll et al. | |
| 2017/0354593 | A1* | 12/2017 | Majumdar | A61K 31/439 |

FOREIGN PATENT DOCUMENTS

| | | | |
|---|---|---|---|
| CN | 102762543 A | 10/2012 | |
| CN | 103957701 A | 7/2014 | |
| EP | 2865369 A1 | 4/2015 | |
| JP | 2004501750 A | 1/2004 | |
| JP | 2007319124 A | 12/2007 | |
| JP | 2011527288 A | 10/2011 | |
| WO | 2002000557 A2 | 1/2002 | |
| WO | 2005085216 A1 | 9/2005 | |
| WO | 2007079162 A1 | 7/2007 | |
| WO | 2008122375 A2 | 10/2008 | |
| WO | 2009002809 A2 | 12/2008 | |
| WO | 2009003075 A1 | 12/2008 | |
| WO | 2009024541 A2 | 2/2009 | |
| WO | WO-2009024541 A2 * | 2/2009 | ............ A01N 43/80 |
| WO | 2009080250 A2 | 7/2009 | |
| WO | 2010003263 A2 | 1/2010 | |
| WO | 2010070068 A2 | 6/2010 | |
| WO | 2010079077 A1 | 7/2010 | |
| WO | 2011075591 A1 | 6/2011 | |
| WO | 2011092287 A1 | 8/2011 | |
| WO | 2011124998 A1 | 10/2011 | |
| WO | 2012155352 A1 | 11/2012 | |
| WO | 2012155676 A1 | 11/2012 | |
| WO | 2012158396 A1 | 11/2012 | |
| WO | 2013026695 A1 | 2/2013 | |
| WO | 2013026931 A1 | 2/2013 | |
| WO | 2015048371 A1 | 4/2015 | |

(Continued)

OTHER PUBLICATIONS

European Search Report for EP15173454.8 dated Dec. 23, 2015, 6 pages.

Gassel, M et al, The novel isoxazoline ectoparasiticide fluralaner: Selective inhibition of arthropod g-aminobutyric acid- and L-glutamate-gated chloride channels and insecticidal/acaricidal activity, Insect Biochemistry and Molecular Biology, 2014, pp. 111-124, vol. 45.

Guideline On Test Procedures and Acceptance Criteria for New Veterinary Drug Substances and New Medicinal Products: Chemical Substances, European Medicines Agency Veterinary Medicines and Inspections 7 Westferry Circus, Canary Wharf, London, E14 4HB, UK Nov. 15, 2005, Section 3.3.2, pp. 11-12.

ISR for application PCT/EP2016/064449 mailed on Sep. 8, 2016, 3 pages.

(Continued)

*Primary Examiner* — Jared Barsky
(74) *Attorney, Agent, or Firm* — David J. Kerwick

(57) ABSTRACT

For the prevention of parasite infestation of animals, an isoxazoline can be administered by drinking water route. However the inventors have found that when the drinking water is sanitized, for instance by using hypochlorite, the isoxazoline becomes degraded. Surprisingly, the isoxazoline can be protected from degradation by the use of a vitamin E. A pharmaceutical composition can now be prepared containing a concentrated solution of the isoxazoline in a solvent and co-solvent, with vitamin E. The composition can be diluted in drinking water, even when sanitized, to prepare medicated drinking water for animals. This way an antiparasitic treatment can be mass-administered, leading to a highly effective reduction of the parasite infestation of an animal, and its surroundings.

2 Claims, No Drawings

(56) References Cited

FOREIGN PATENT DOCUMENTS

| WO | 2015066277 A1 | 5/2015 |
|---|---|---|
| WO | 2015086551 A1 | 6/2015 |
| WO | 2015091898 A1 | 6/2015 |
| WO | 2015091900 A1 | 6/2015 |

OTHER PUBLICATIONS

Shoop, W et al, Discovery and mode of action of afoxolaner, a new newisoxazoline parasiticide for dogs, Veterinary Parasitology, 2014, pp. 179-189, vol. 201, Elsevier.
U.S. Appl. No. 16/523,780, filed Jul. 26, 2019.
U.S. Appl. No. 15/735,252, filed Dec. 11, 2017.

* cited by examiner

ISOXAZOLINE SOLUTION CONTAINING VITAMIN E FOR USE WITH SANITIZED DRINKING WATER

CROSS-REFERENCE TO RELATED APPLICATIONS

This application is a continuation of U.S. application Ser. No. 16/523,780, filed Jul. 26, 2019, which is a continuation of U.S. application Ser. No. 15/735,252, filed Dec. 11, 2017, which was the national stage entry under 35 U.S.C. § 371 of PCT/EP2016/064449, filed on Jun. 22, 2016, which claims priority to EP Application No. EP15173454.8, filed on Jun. 23, 2015, the entire contents of each of these applications are hereby incorporated by reference.

The present invention relates to the fields of veterinary parasitology and -pharmacology, specifically to the treatment or prevention of parasite infestation of non-human animals. In particular the invention relates to a pharmaceutical composition comprising an isoxazoline, a solvent and a co-solvent; to medicated drinking water comprising this pharmaceutical composition; to methods for the preparation of the pharmaceutical composition and of the medicated drinking water; to (medical) uses of the pharmaceutical composition and of the medicated drinking water; to the stabilisation of an isoxazoline in medicated drinking water comprising a water sanitizer; to a container comprising the pharmaceutical composition; and to a kit comprising the container.

Isoxazoline substituted benzamide derivatives were first described in WO 2005/085216 (Nissan Chem. Ind. Ltd.), as pesticides with potential for veterinary insecticidal- and acaricidal use, and subsequently their use as parasiticides has been further developed. These hydrophobic compounds contain a 5 membered isoxazole ring structure, which is covalently bound to other aryl or heteroaryl systems in position 3 and 5, and which can each contain further substituents or more or less extensive side chains. The isoxazolines possess at least one chiral centre at position 5 of the isoxazoline ring. While the S-enantiomer seems to provide the parasiticidal activity, but often a racemic mixture is used. Meanwhile many variants of isoxazoline pesticides have been described, for example in: WO 2007/079162, WO 2008/122375, WO 2009/002809, WO 2009/024541, WO 2009/080250, WO 2010/070068, WO 2010/079077, WO 2011/075591, WO 2011/124998, WO 2012/155352, WO 2012/155676, WO 2012/158396, WO 2015/048371, WO 2015/066277, and EP 2865369. Several isoxazoline parasiticides were described specifically for veterinary use in the prevention or treatment of infestations by ectoparasites. Examples are: Fluralaner (CAS registry number: 864731-61-3), Afoxolaner (CAS RN: 1093861-60-9), Lotilaner (CAS RN: 1369852-71-0), and Sarolaner (CAS RN: 1398609-39-6).

These isoxazolines are known to be very effective parasiticides, mainly by their effect on the nervous system by blocking of the GABA-gated chloride channel of arthropods (see Gassel et al., 2014, Insect Biochem. Mol. Biol., vol. 45, p. 111; and: Shoop et al., 2014, Vet. Paras., vol. 201, p. 179). Currently two formulations are commercially available: Bravecto™ (Fluralaner—Merck/MSD Animal Health), and NexGard™ (Afoxolaner—Merial), which both have been registered specifically for oral administration to dogs for the prevention of fleas and ticks. After oral uptake via a soft-chew tablet, the active is distributed systemically, and upon a bite an ectoparasite ingests a lethal dose of the parasiticide.

For animals other than dogs, the oral administration route is equally effective, however for animals which are reared in intensive farming operations such as pigs, cattle and poultry, a method of administration more suitable for mass application is preferred, such as administration by drinking water. In that respect PCT/EP2014/078634, the content of which is hereby incorporated by reference, describes a formulation comprising an isoxazoline, a solvent and a surfactant which provides a composition that can effectively be administered via the existing drinking water system and water medication equipment, without significant segregation or sedimentation of the active compound.

Patent application PCT/EP2014/078636 the content of which is hereby incorporated by reference, describes advantageous use of such a composition for the treatment of poultry via drinking water, especially against parasitic arthropods.

Many types of animal parasites are known; next to internal- or endoparasites, ectoparasites are relevant as they are more readily apparent on the affected animal, and their effects on the welfare and economic performance of animals can be considerable. Ectoparasites are very diverse, but the most relevant pests are arthropods, for example: insects like flies, fleas, lice, bugs and mosquitoes, or arachnids like ticks and mites. Many ectoparasites, in one or more stages of their development, feed on tissue, blood or other body fluids from a host. Negative effects can vary from a simple annoyance to a cause of death. This is because the parasite-host contact involves a variety of mechanical and biological interactions: the ectoparasite's piercing of the skin may cause a rash, an inflammation, or a secondary infection; the repeated blood consumption by thousands of ectoparasites over time may cause a host to become anaemic; and also the parasite may be a vector for pathogens (bacteria, *Rickettsia*, viruses, protozoa or helminths) that can infect the host from the parasite's mouth-parts, saliva, or its faeces.

One of the advantageous uses described in PCT/EP2014/078634 and PCT/EP2014/078636, is the prevention or treatment of infestation of poultry with mites such as *Dermanyssus gallinae* (poultry red mite), *Ornithonyssus sylviarum* (Northern fowl mite), and *O. bursa* (tropical fowl mite). These live and develop in poultry houses and -farms, and at night crawl onto sitting birds (or remain stationary: *O. sylviarum* and *O. bursa*) and suck blood. Apart from a danger for transferring pathogens, a heavy infestation with mites can cause the birds to become anaemic. Not only is such an infestation a severe discomfort to the animals, it will also lead to a reduction in economic production levels, such as feed conversion, daily weight gain, and egg production, but also to increased costs for veterinary care and disinfection. In addition, heavy mite infestations will also affect persons handling the birds, as they may be bitten as well.

Conventional methods of extermination of mite infestation employ synthetic organic chemicals such as pyrethroids, organophosphates, carbamates or spinosad, to decontaminate the poultry house or the birds themselves e.g. by spray, fog, or dust. However, because mites are very small and hide in cracks, such treatments have only been moderately effective. In addition, these chemical treatments are being increasingly scrutinised due to development of resistance in the parasites, as well as out of concerns over environmental- and occupational safety. Therefore an alternative, and more effective way to treat and prevent mite infestation in poultry farming is required.

In several countries the drinking water used for animal farming is obtained from a variety of sources, such as tap water, but more likely from groundwater-wells, lakes, or creeks. Such water will be of moderate- and variable quality, and may contain a number of contaminants. Amongst others, the use of these natural water sources may expose the animals to several potentially pathogenic micro-organisms such as viruses, bacteria, parasites, and unicellular organisms. To provide some level of decontamination, animal drinking water is often given a sanitizing treatment. Options include physical decontamination using filtration, heat or UV light, but mostly chemical decontamination is applied. Examples are the addition of ozone, hydrogen peroxide, or compounds containing halogen-atoms, such as bromine, iodine, or chlorine. These chemical decontaminants provide oxidising radicals to the drinking water that effectively inactivate microorganisms present. Such an oxidizing sanitizer can be added to the drinking water e.g. using a dosing pump directly on the main line, or via the pre-treatment of water in a storage tank.

Especially chlorine containing compounds have been found to be cheap and effective, such as hypochlorite(aq) (ClO−; CAS RN: 14380-61-1) or chlorine dioxide ($ClO_2$; CAS RN: 10049-04-4). As hypochlorite salts are unstable under influence of pH and temperature, this is commercially available as hypochlorite solution in water, or: bleach. While levels of chlorination of animal drinking water up to 100 parts per million (ppm) are feasible, typical levels used for sanitising animal drinking water are between 1 and 10 ppm, measured in level of residual chlorine at the most distant point in the waterline.

Some prior art publications generally describe oral administration of an isoxazoline (WO 2009/003075), or administration via drinks (WO 2009/003075, WO 2010/070068, WO 2013/026695, WO 2013/026931), but none describes use in medicated drinking water containing a water sanitizer, or provide for any protection from degradation of the isoxazoline under such conditions.

For the treatment of parasite infestation of animals by isoxazoline parasiticides via drinking water administration, pharmaceutical compositions that can be used for preparing such medicated drinking water should provide maximum availability of the active compound, and no segregation or sedimentation of the active compound in the drinking water system, medication pumps, nipples, cups etc. Also these compositions should allow a homogeneous distribution and easy dosing of the active compound in the drinking water. In addition, such compositions should protect the active compound from degradation, both when in the concentrated pharmaceutical composition itself, as well as in dilution in drinking water of all types, whether that is sanitised or not. No such pharmaceutical compositions have yet been described.

It is therefore an object of the present invention to overcome one or more disadvantages in the prior art, and to accommodate to this need in the field by providing for the first time, a pharmaceutical composition comprising a solution of an isoxazoline that can be used effectively for prevention or treatment of parasite infestation of animals, by administration via drinking water, even when that water contains a water sanitizer.

The administration of an isoxazoline solution to poultry via drinking water was found to be highly effective against red mite: after a single administration at 0.5 mg isoxazoline/kg, mite mortality and mite inhibition levels up to 100% could be reached for D. gallinae, at 24 hours after challenge infestation, and even levels of 99% inhibition of red mites for 15 days. Similarly, reduction of Northern fowl mite infestations of more than 90% was found for at least 19 days. By such inhibition of parasite infestation, the lifecycle of such parasitic arthropods can be interrupted and the establishing of a new significant population in the house or farm can be prevented for a whole animal production cycle.

However, the inventors were disappointed to learn this did not work for all types of drinking water. After further investigation, they discovered there was a negative effect correlated to the presence of water-sanitizers in the drinking water. Indeed: when the drinking water used contained an oxidising water sanitizer, the isoxazoline diluted in such water became degradated, leading to loss of activity. Without guidance from the prior art they then had to devise a way to prevent such degradation of the active compound in dilution, while maintaining its full availability and optimal effectiveness.

This was not at all straightforward and required making several unobvious choices and selections. This is apparent from the results of testing several different compounds both hydrophilic and hydrophobic, for a protective effect. While occasionally one of the tested protectors would perform well in preventing isoxazoline degradation in sanitised drinking water, however the compound was then found lacking in other relevant criteria, such as for example in providing long term stability to the pharmaceutical composition itself that is the concentrate which can be diluted in drinking water, to prepare the medicated drinking water. Examples are described hereinafter.

The inventors were therefore surprised to find that vitamin E, was able to effectively prevent isoxazoline degradation in sanitised drinking water, while maintaining other favourable characteristics, such as availability and effectivity in dilution, and the long-term stability of the pharmaceutical composition concentrate. The excellent dispersion in drinking water was all the more surprising in view of the fatty nature of vitamin E; in fact in the dilution in sanitised drinking water, the isoxazoline now is protected for at least 24 hours. Also the concentrated solution of the pharmaceutical composition as described herein, has at least 18 months of shelf-life.

In view of the potentially large scale at which such an antiparasitic therapy may be used in intensive animal farming, these effects and improvements are significant, and represent a surprising technical effect that has great commercial significance. Therefore, in this way the object of the invention was met, and consequently disadvantages of the prior art were overcome.

It is currently not known exactly why a vitamin E can prevent the degradation of an isoxazoline when diluted in sanitised drinking water, without interfering with the distribution of the compound in dilution, or with the long shelf-life of the pharmaceutical composition. Although the inventors do not want to be bound by any theory or model that might explain these observations, they speculate that in particular the nitrogen atoms in the side chain of the isoxazoline (in the groups T and Q of an isoxazoline as defined herein) are sensitive to reaction with oxidising sanitizers in the drinking water. The vitamin E probably prevents oxidizing radicals in the sanitised drinking water from attacking and degradating the isoxazoline at these groups. Also, the vitamin E can apparently mix very well with the other components in the pharmaceutical composition, and can mix well with drinking water.

Therefore in one aspect the invention relates to a pharmaceutical composition comprising an isoxazoline in a pharmaceutically acceptable solvent and a co-solvent, the isoxazoline is the compound as defined herein, characterised in that the composition comprises a vitamin E.

The pharmaceutical composition according to the invention is a concentrated solution (or solvate) of an isoxazoline in a solvent and a co-solvent, which concentrate can be used for the preparation of a medicated drinking water for animal use, by its dilution into drinking water, even when that contains a water sanitizer. This will provide the animals with an effective dose of the active parasiticidal compound: the isoxazoline, upon their ingestion of the medicated drinking water.

As used herein and throughout, 'sanitised drinking water' refers to drinking water comprising a water sanitizer. However, and as the skilled person will understand, the concentration of water sanitizer in the drinking water may vary in practice, depending e.g. on the time since the sanitizer was added, and on the point of sampling in the drinking water installation.

A 'pharmaceutically acceptable solvent' is a solvent that is capable of dissolving and keeping dissolved, a practical concentration of the isoxazoline of the invention, and in addition is acceptable for veterinary use, in particular for oral administration to food animals. Further the solvent is compatible with the other constituents of the pharmaceutical composition according to the invention, and does not negatively affect the palatability of the drinking water in which it may be dissolved. Such solvents are well-known in the art, and are for instance described in handbooks such as "Remington: The Science and Practice of Pharmacy" (20th Ed., 2000, ISBN: 0683306472). Also, suitable solvents are described in regulatory documents and Pharmacopoeia's. These solvents are commercially available from a large number of suppliers, and at a desired purity and quality.

A 'co-solvent' is an additional pharmaceutically acceptable solvent. Such co-solvent can assist in solubilising the isoxazoline in the pharmaceutical composition according to the invention.

The co-solvent should be compatible with the other components of the pharmaceutical composition according to the invention, as well as be pharmaceutically acceptable for oral use in food-animals. Such co-solvents are well-known in the art; examples are: ethyl lactate, a pyrrolidone solvent such as 2 pyrrole, or a surfactant such as a polysorbate, or mixtures thereof.

The term 'vitamin E' refers to a well-known family of compounds with related chemical structure that are fat soluble. The family comprises two main groups of compounds: tocopherols and tocotrienols. Vitamin E is commonly available as an oily substance, which can be derived from vegetable materials such as seeds, nuts, fruits or leaves, from fatty meats, but may also be produced synthetically. As a vitamin it provides a variety of health effects, especially to the skin.

Included in the definition of vitamin E are natural, synthetic or semi-synthetic forms of vitamin E, mixtures of two or more forms, and derivatives with attached groups such as such as esters (e.g. of acetate or succinate), polyethylene glycol, nicotin, or linolin.

For use in the invention, the 'isoxazoline' is the following compound:

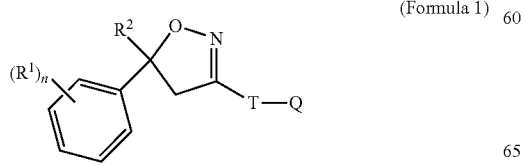

(Formula 1)

wherein
$R^1$=halogen, $CF_3$, $OCF_3$, or CN;
n=integer from 0 up to and including 3;
m=1 or 2;
$R^2$=$C_1$-$C_3$haloalkyl;
T=ring structure: 5-, or 6-membered, or bicyclic, which is optionally substituted by one or more radicals Y;
Y=methyl, halomethyl, halogen, CN, $NO_2$, $NH_2$—C≡S, or two adjacent radicals Y together form a chain;
Q=X—$NR^3R^4$, $NR^5$—$NR^6$—X—$R^3$, X—$R^3$, or a 5-membered N-heteroaryl ring, which is optionally substituted by one or more radicals;
X=$CH_2$, $CH(CH_3)$, $CH(CN)$, CO, CS;
$R^3$=hydrogen, methyl, haloethyl, halopropyl, halobutyl, methoxymethyl, methoxyethyl, halomethoxymethyl, ethoxymethyl, haloethoxymethyl, propoxymethyl, ethylaminocarbonylmethyl, ethylaminocarbonylethyl, dimethoxyethyl, propynylaminocarbonylmethyl, N-phenyl-N-methyl-amino, haloethylaminocarbonylmethyl, haloethylaminocarbonylethyl, tetrahydrofuryl, methylaminocarbonylmethyl, (N,N-dimethylamino)-carbonylmethyl, propylaminocarbonylmethyl, cyclopropylaminocarbonylmethyl, propenylaminocarbonylmethyl, haloethylaminocarbonylcyclopropyl, alkylsulfanylalkyl, alkylsulfinylalkyl, alkylsulfonylalkyl, cycloalkyl,

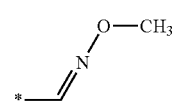

R³-1

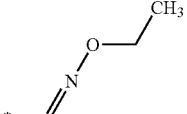

R³-2

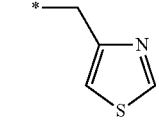

R³-3

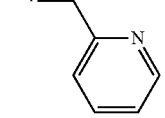

R³-4

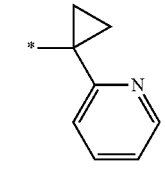

R³-5

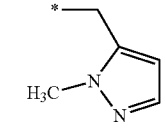

R³-6

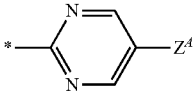

R³-7

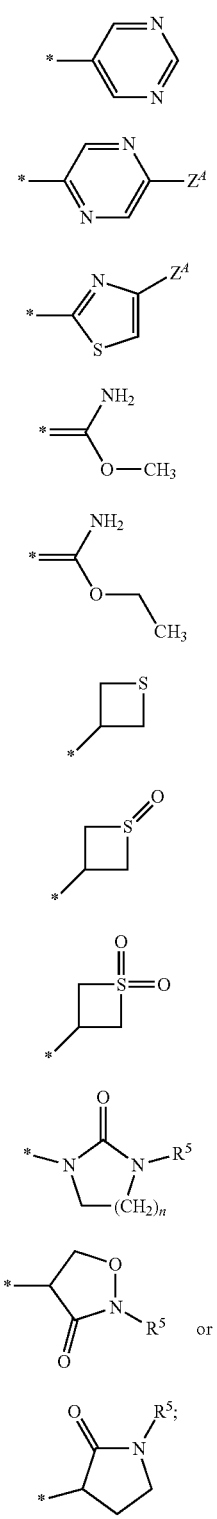

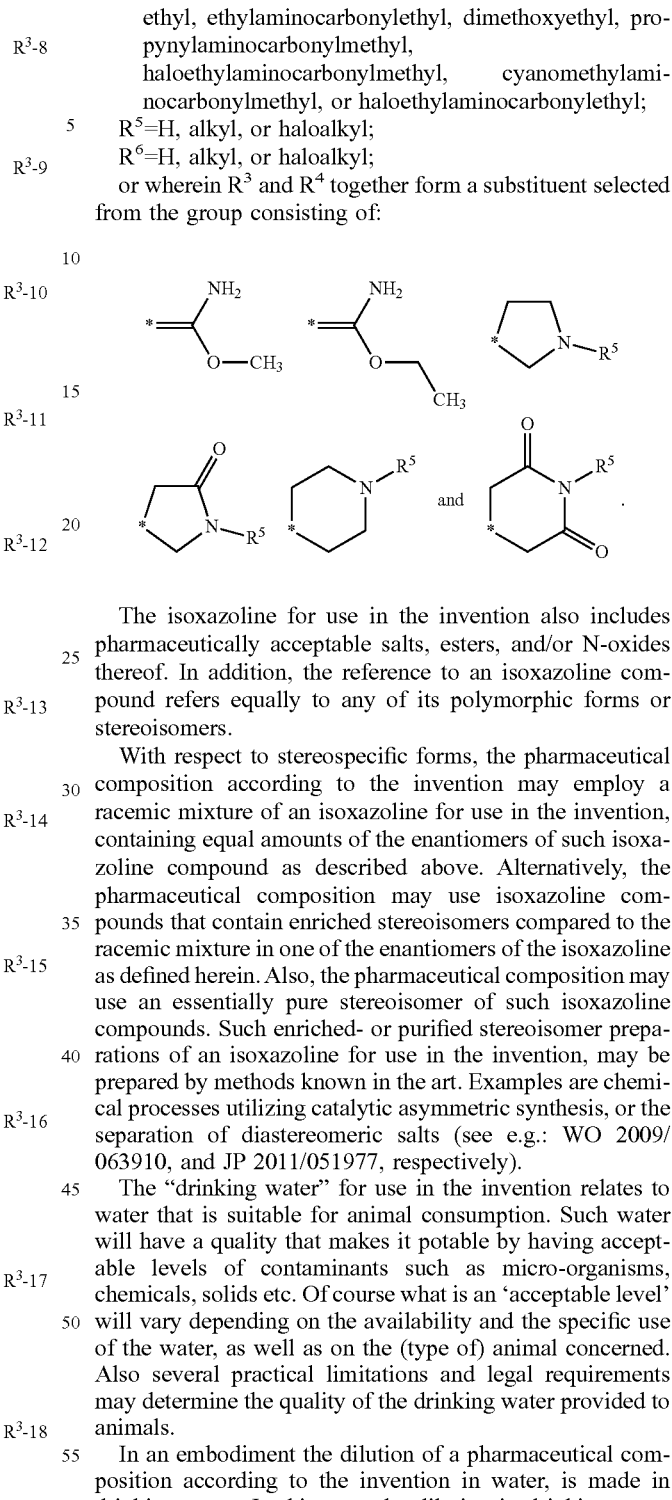

wherein
$Z^4$=hydrogen, halogen, cyano, or halomethyl (CF$_3$);
$R^4$=hydrogen, ethyl, methoxymethyl, halomethoxymethyl, ethoxymethyl, haloethoxymethyl, propoxymethyl, methylcarbonyl, ethylcarbonyl, propylcarbonyl, cyclopropylcarbonyl, methoxycarbonyl, methoxymethylcarbonyl, aminocarbonyl, ethylaminocarbonylmethyl, ethylaminocarbonylethyl, dimethoxyethyl, propynylaminocarbonylmethyl, haloethylaminocarbonylmethyl, cyanomethylaminocarbonylmethyl, or haloethylaminocarbonylethyl;
$R^5$=H, alkyl, or haloalkyl;
$R^6$=H, alkyl, or haloalkyl;
or wherein $R^3$ and $R^4$ together form a substituent selected from the group consisting of:

The isoxazoline for use in the invention also includes pharmaceutically acceptable salts, esters, and/or N-oxides thereof. In addition, the reference to an isoxazoline compound refers equally to any of its polymorphic forms or stereoisomers.

With respect to stereospecific forms, the pharmaceutical composition according to the invention may employ a racemic mixture of an isoxazoline for use in the invention, containing equal amounts of the enantiomers of such isoxazoline compound as described above. Alternatively, the pharmaceutical composition may use isoxazoline compounds that contain enriched stereoisomers compared to the racemic mixture in one of the enantiomers of the isoxazoline as defined herein. Also, the pharmaceutical composition may use an essentially pure stereoisomer of such isoxazoline compounds. Such enriched- or purified stereoisomer preparations of an isoxazoline for use in the invention, may be prepared by methods known in the art. Examples are chemical processes utilizing catalytic asymmetric synthesis, or the separation of diastereomeric salts (see e.g.: WO 2009/063910, and JP 2011/051977, respectively).

The "drinking water" for use in the invention relates to water that is suitable for animal consumption. Such water will have a quality that makes it potable by having acceptable levels of contaminants such as micro-organisms, chemicals, solids etc. Of course what is an 'acceptable level' will vary depending on the availability and the specific use of the water, as well as on the (type of) animal concerned. Also several practical limitations and legal requirements may determine the quality of the drinking water provided to animals.

In an embodiment the dilution of a pharmaceutical composition according to the invention in water, is made in drinking water. In this way, the dilution in drinking water produces a medicated drinking water.

The 'medicated drinking water' for use in the invention is drinking water that contains a pharmaceutically active compound and water.

In an embodiment of the pharmaceutical composition according to the invention, the vitamin E is a tocopherol; in a further embodiment the tocopherol is an alpha- or a gamma-tocopherol; more preferred is an alpha-tocopherol. Alpha-tocopherol (CAS RN: 59-02-9) is generally available commercially.

The inventors found that alpha-tocopherol was very effective in preventing degradation of an isoxazoline in sanitised drinking water, while having no negative effect on the dispersion of the compound in dilution, or on the stability of the concentrated solution itself Therefore, in an embodiment of the pharmaceutical composition according to the invention, the vitamin E is alpha-tocopherol.

Weight amounts of the vitamin E in the pharmaceutical composition according to the invention, are between about 1 and about 20% w/w of the final pharmaceutical composition according to the invention.

Preferred amounts of the vitamin E are between about 2 and about 15%, more preferably between 3-12, 4-10, or even between about 5 and about 9% w/w of the final pharmaceutical composition according to the invention, in this order of preference. Particularly preferred amounts are about 66 or about 82 mg vitamin E/gram of the final pharmaceutical composition according to the invention.

For use in the invention, an approximate numerical value described as 'about x', refers to a value of x with a margin that is ±10% around that value. Alternatively ±9, 8, 7, 6, 5, 4, 3, 2, or 1% around that value.

The 'final' pharmaceutical composition according to the invention, is the pharmaceutical composition in its complete constitution, in which it is ready for sale and commercial use, and prior to its dilution.

In an embodiment, the pharmaceutically acceptable solvent is an ethoxy-ethanol; in a preferred embodiment, the ethoxy ethanol is a diethylene glycol monoethyl ether (CAS RN: 111-90-0). Such a solvent is available commercially, for instance under the trade name Transcutol™ (Gattefossé, St. Priest, France), and many other names. Particularly preferred are the product types: Transcutol™ V, P and HP.

This solvent demonstrated excellent solubility of the isoxazoline, very precise dosing and homogenous dispersion of the active compound upon dilution in drinking water, and transport through the drinking water installation. Also this solvent is pharmaceutically acceptable in being safe even for oral administration to food-animals.

Amounts of the ethoxy-ethanol in the pharmaceutical composition according to the invention are between about 5% and about 75% w/w of the final pharmaceutical composition according to the invention.

Preferred amounts of the ethoxy-ethanol are between about 10 and about 60%, more preferably between 15-50, 17-40, 19-30, or even between about 20 and about 25% w/w of the final pharmaceutical composition according to the invention, in this order of preference. Particularly preferred amount is about 227 mg ethoxy-ethanol/gram of the final pharmaceutical composition according to the invention.

In an embodiment of the pharmaceutical composition according to the invention, the co-solvent is a surfactant. In this form the co-solvent can assist in the homogenous dispersion of the concentrated solution in drinking water. In a further embodiment the surfactant is a polysorbate.

In a preferred embodiment of the pharmaceutical composition according to the invention the polysorbate is a polyoxyethylene (20) sorbitan monooleate (CAS RN: 9005-65-6), which compound is also known as Polysorbate 80, or for example as the commercial product: Tween™ 80. This is available from a variety of commercial sources.

The inventors speculate that in contact with water the polysorbate surfactant can assist in the creation of microscopic micelles around the isoxazoline compound that is solubilized in the ethoxy-ethanol. This way the surfactant can help to maintain the solubilized isoxazoline compound dispersed in the aqueous environment of a medicated drinking water according to the invention.

Amounts of the polysorbate surfactant in the pharmaceutical composition according to the invention are preferably between about 20% and about 95% w/w of the final pharmaceutical composition according to the invention.

More preferred amounts of the polysorbate surfactant are between about 30 and about 90%, between 40-90, 50-85, 55-80, or even between about 60 and about 75% w/w of the final pharmaceutical composition according to the invention, in this order of preference. Particularly preferred amount is about 681 mg polysorbate surfactant/gram of the final pharmaceutical composition according to the invention.

In an embodiment of the pharmaceutical composition according to the invention, the ratio between the ethoxy-ethanol and polysorbate in the final pharmaceutical composition according to the invention is between about 2:1 and about 1:6; preferably the ratio is between about 1:1 and about 1:5; or even between about 1:2 and about 1:4, in this order of preference.

Particularly preferred is a ratio between the ethoxy-ethanol and polysorbate in the final pharmaceutical composition according to the invention of about 1:3, meaning there is about 3× more polysorbate present than ethoxy-ethanol. This ratio has been shown to result in especially homogenous dispersions of the pharmaceutical composition according to the invention in drinking water. Also, at this ratio the vitamin E is incorporated well into the pharmaceutical composition according to the invention, and mixes well with the drinking water.

Therefore, in an embodiment, the pharmaceutical composition according to the invention comprises an amount of a vitamin E at between about 5 and about 9%, an ethoxy-ethanol at between about 20 and about 25%, and a polysorbate at between about 60 and about 75%, all in % w/w of the final pharmaceutical composition according to the invention.

In an embodiment, the pharmaceutical composition according to the invention may comprise other non-active compounds or excipients that are known to the skilled person e.g. as described in "Remington" (supra), for instance to enhance convenience, stability, or pharmacological effectiveness.

In an embodiment, the pharmaceutical composition according to the invention may comprise other active compounds, e.g. other antiparasitic compounds, such as moxidectin, ivermectin, a benzamidazole, or an antibiotic such as a macrocyclic lactone, etc. Of course the combination should be pharmaceutically acceptable for oral administration via drinking water to food animals. Also the combination should not interfere with the antiparasitic effect of the oxazoline for use in the present invention.

In an embodiment, the pharmaceutical composition according to the invention may comprise an antifoaming agent, such as for example simethicone, sodium oleate, sodium caprylate, or mixtures thereof.

The antifoaming agent is present in sufficient concentration to prevent foam formation when the pharmaceutical composition is diluted and mixed into drinking water. The antifoaming agent may be present at an amount of between about 0.0001% w/w and about 0.1% w/w, preferably between about 0.001% w/w and about 0.01% w/w of the final pharmaceutical composition according to the invention. Preferred antifoaming agent is simethicone; simethicone is for example a siloxane emulsion such as Q7-2243 (Dow Corning, USA).

In an embodiment, the pharmaceutical composition according to the invention may comprise a preservative.

Such preservatives are known to those skilled in the art, and may be applied to allow multi-use dosage forms. Examples of preservatives are e.g. benzyl alcohol, butylparaben sodium salt, methylparaben sodium salt, propylparaben sodium salt, or mixtures thereof. A preservative may be present at an amount of between about 0.01% w/w and about 3% w/w of the final pharmaceutical composition according to the invention. Preferred preservative is benzyl alcohol.

In an embodiment of an isoxazoline for use in the invention, T is selected from

T-1
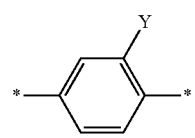

T-2
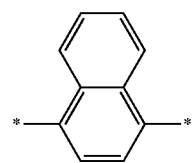

T-3
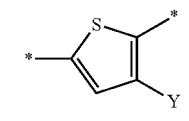

T-4
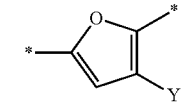

T-5
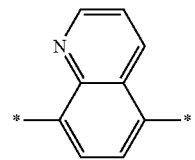

T-6
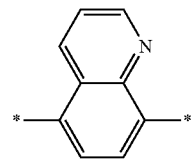

T-7
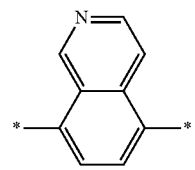

T-8
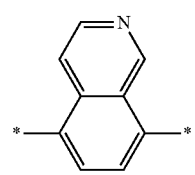

-continued

T-9
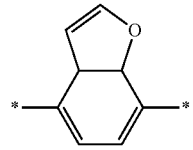

T-10
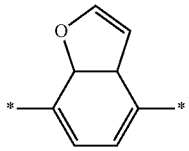

T-11
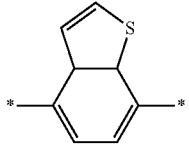

T-12
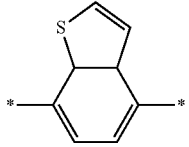

T-13
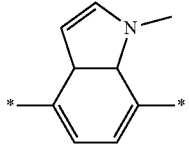

T-14
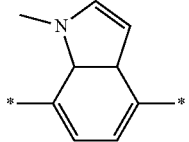

T-15
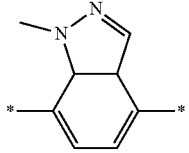

T-16
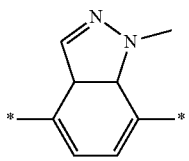

T-17
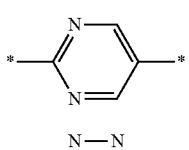

T-18
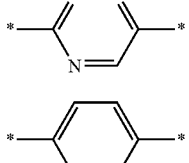

T-19

-continued
T-20
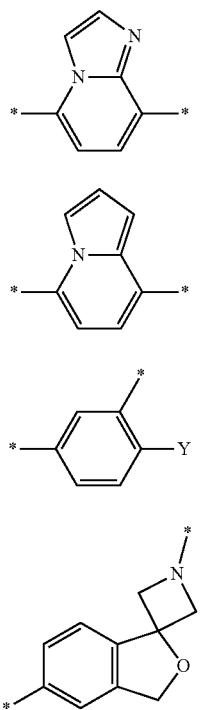
T-21
T-22
T-23
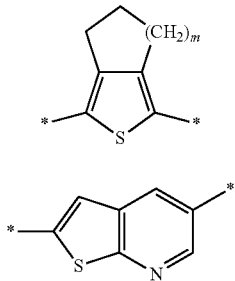
T-24
T-25
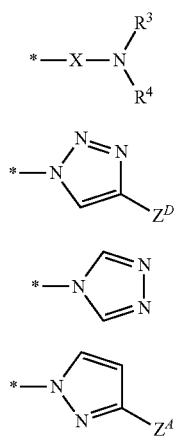
wherein in T-1, T-3 and T-4, the radical Y=hydrogen, halogen, methyl, halomethyl, ethyl, or haloethyl.
In an embodiment of an isoxazoline for use in the invention, Q is selected from
Q-1
*—X—N(R³)(R⁴)
Q-2
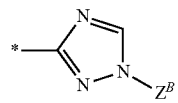
Q-3
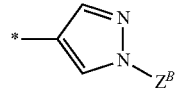
Q-4
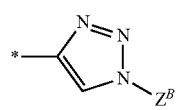
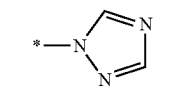
-continued
Q-5
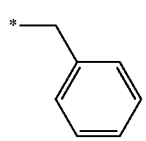
Q-6
Q-7
Q-8
Q-9
wherein R³, R⁴, X and $Z^A$ are as defined above, and
$Z^B=$
$Z^B$-1
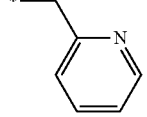
$Z^B$-2
$Z^B$-3
$Z^B$-4
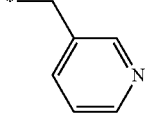
$Z^B$-5
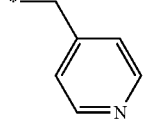
$Z^B$-6
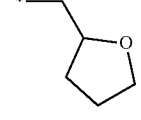
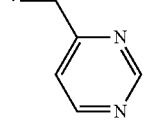

-continued

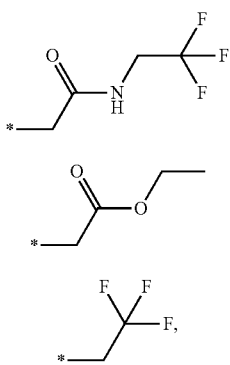
Z^B-7

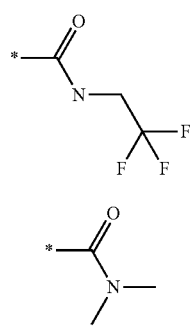
Z^B-8

Z^D =

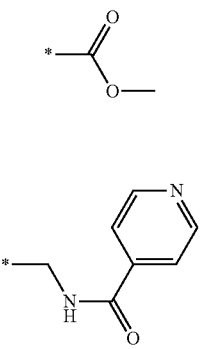
Z^D-1

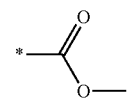
Z^D-2

Z^D-3

Z^D-4

Z^D-5

Z^D-6

In an embodiment an isoxazoline for use in the invention is as presented in Table 1.

TABLE 1

| $(R^1)_n$ | $R^2$ | $R^3$ | $R^4$ | T | Y | Q | Z | X |
|---|---|---|---|---|---|---|---|---|
| 3-Cl, 5-Cl | $CF_3$ | $CH_2CF_3$ | H | T-2 | — | Q-1 | — | CO |
| 3-Cl, 5-Cl | $CF_3$ | $CH_2CH_3$ | H | T-2 | — | Q-1 | — | CO |
| 3-Cl, 5-Cl | $CF_3$ | $CH_2CH_2OCH_3$ | H | T-2 | — | Q-1 | — | CO |
| 3-Cl, 5-Cl | $CF_3$ | $CH_2C(O)NHCH_2CF_3$ | H | T-2 | — | Q-1 | — | CO |
| 3-Cl, 5-Cl | $CF_3$ | $CH_2C(O)NHCH_2CH_3$ | H | T-2 | — | Q-1 | — | CO |
| 3-$CF_3$, 5-$CF_3$ | $CF_3$ | $CH_2C(O)NHCH_2CF_3$ | H | T-2 | — | Q-1 | — | CO |
| 3-$CF_3$, 5-$CF_3$ | $CF_3$ | $CH_2C(O)NHCH_2CH_3$ | H | T-2 | — | Q-1 | — | CO |
| 3-$CF_3$, 5-Cl | $CF_3$ | $CH_2C(O)NHCH_2CF_3$ | H | T-2 | — | Q-1 | — | CO |
| 3-$CF_3$, 5-Cl | $CF_3$ | $CH_2C(O)NHCH_2CH_3$ | H | T-2 | — | Q-1 | — | CO |
| 3-Cl, 5-Cl | $CF_3$ | — | | T-2 | — | Q-6 | $Z^B$-7 | CO |
| 3-Cl, 5-Cl | $CF_3$ | — | | T-2 | — | Q-7 | $Z^B$-7 | CO |
| 3-Cl, 5-Cl | $CF_3$ | — | | T-2 | — | Q-5 | $Z^B$-7 | CO |
| 3-Cl, 5-Cl | $CF_3$ | — | | T-2 | — | Q-2 | $Z^D$-1 | CO |
| 3-Cl, 5-Cl | $CF_3$ | $CH_2C(O)NHCH_2CF_3$ | H | T-3 | $CH_3$ | Q-1 | — | CO |
| 3-Cl, 5-Cl | $CF_3$ | $CH_2C(O)NHCH_2CC$ | H | T-3 | $CH_3$ | Q-1 | — | CO |
| 3-Cl, 5-Cl | $CF_3$ | $CH_2C(O)NHCH_2CN$ | H | T-3 | $CH_3$ | Q-1 | — | CO |
| 3-Cl, 5-Cl | $CF_3$ | $CH_2C(O)NHCH_2CH_3$ | H | T-3 | $CH_3$ | Q-1 | — | CO |
| 3-$CF_3$, 5-$CF_3$ | $CF_3$ | $CH_2C(O)NHCH_2CF_3$ | H | T-3 | $CH_3$ | Q-1 | — | CO |
| 3-$CF_3$, 5-$CF_3$ | $CF_3$ | $CH_2C(O)NHCH_2CH_3$ | H | T-3 | $CH_3$ | Q-1 | — | CO |
| 3-Cl, 4-Cl, 5-Cl | $CF_3$ | $CH_2C(O)NHCH_2CF_3$ | H | T-3 | $CH_3$ | Q-1 | — | CO |
| 3-Cl, 4-Cl, 5-Cl | $CF_3$ | $CH_2C(O)NHCH_2CH_3$ | H | T-3 | $CH_3$ | Q-1 | — | CO |
| 3-Cl, 4-F, 5-Cl | $CF_3$ | $CH_2C(O)NHCH_2CF_3$ | H | T-3 | $CH_3$ | Q-1 | — | CO |
| 3-Cl, 4-F, 5-Cl | $CF_3$ | $CH_2C(O)NHCH_2CH_3$ | H | T-3 | $CH_3$ | Q-1 | — | CO |
| 3-Cl, 5-Cl | $CF_3$ | $CH_2C(O)NHCH_2CF_3$ | H | T-20 | — | Q-1 | — | CO |
| 3-Cl, 5-Cl | $CF_3$ | $CH_2C(O)NHCH_2CH_3$ | H | T-20 | — | Q-1 | — | CO |

TABLE 1-continued

| (R¹)ₙ | R² | R³ | R⁴ | T | Y | Q | Z | X |
|---|---|---|---|---|---|---|---|---|
| 3-CF₃, 5-CF₃ | CF₃ | CH₂C(O)NHCH₂CF₃ | CH₃ | T-20 | — | Q-1 | — | CO |
| 3-CF₃, 5-CF₃ | CF₃ | CH₂C(O)NHCH₂CH₃ | CH₃ | T-20 | — | Q-1 | — | CO |
| 3-CF₃, 5-CF₃ | CF₃ | CH₂C(O)NHCH₂CF₃ | H | T-20 | — | Q-1 | — | CO |
| 3-CF₃, 5-CF₃ | CF₃ | CH₂C(O)NHCH₂CH₃ | H | T-20 | — | Q-1 | — | CO |
| 3-CF₃, 5-CF₃ | CF₃ | CH₂C(O)NHCH₂CF₃ | H | T-21 | — | Q-1 | — | CO |
| 3-CF₃, 5-CF₃ | CF₃ | CH₂C(O)NHCH₂CH₃ | H | T-21 | — | Q-1 | — | CO |
| 3-Cl, 5-Cl | CF₃ | CH₂C(O)NHCH₂CF₃ | H | T-21 | — | Q-1 | — | CO |
| 3-Cl, 5-Cl | CF₃ | CH₂C(O)NHCH₂CH₃ | H | T-21 | — | Q-1 | — | CO |
| 3-Cl, 5-Cl | CF₃ | CH₂CH₂SCH₃ | H | T-21 | — | Q-1 | — | CO |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | CO |
| 3-Cl, 5-Cl | CF₃ | CH₂C(O)NHCH₂CH₃ | H | T-1 | CH₃ | Q-1 | — | CO |
| 3-Cl, 5-Cl | CF₃ | R³-1 (Z) | H | T-1 | CH₃ | Q-1 | — | CO |
| 3-Cl, 5-Cl | CF₃ | R³-1 (E) | H | T-1 | CH₃ | Q-1 | — | CO |

In an embodiment an isoxazoline for use in the invention is as presented in Table 2.

TABLE 2

| (R¹)ₙ | R² | R³ | R⁴ | T | Y | Q | Z | X |
|---|---|---|---|---|---|---|---|---|
| 3-Cl, 5-Cl | CF₃ | CH₂CF₃ | H | T-2 | — | Q-1 | — | CO |
| 3-Cl, 5-Cl | CF₃ | CH₂CH₃ | H | T-2 | — | Q-1 | — | CO |
| 3-Cl, 5-Cl | CF₃ | CH₂CH₂OCH₃ | H | T-2 | — | Q-1 | — | CO |
| 3-Cl, 5-Cl | CF₃ | CH₂C(O)NHCH₂CF₃ | H | T-2 | — | Q-1 | — | CO |
| 3-CF₃, 5-CF₃ | CF₃ | CH₂C(O)NHCH₂CF₃ | H | T-2 | — | Q-1 | — | CO |
| 3-CF₃, 5-Cl | CF₃ | CH₂C(O)NHCH₂CF₃ | H | T-2 | — | Q-1 | — | CO |
| 3-Cl, 5-Cl | CF₃ | — | — | T-2 | — | Q-6 | Z^B-7 | |
| 3-Cl, 5-Cl | CF₃ | — | — | T-2 | — | Q-7 | Z^B-7 | |
| 3-Cl, 5-Cl | CF₃ | — | — | T-2 | — | Q-5 | Z^B-7 | |
| 3-Cl, 5-Cl | CF₃ | — | — | T-2 | — | Q-2 | Z^D-1 | |
| 3-Cl, 5-Cl | CF₃ | CH₂C(O)NHCH₂CF₃ | H | T-3 | CH₃ | Q-1 | — | CO |
| 3-Cl, 5-Cl | CF₃ | CH₂C(O)NHCH₂CC | H | T-3 | CH₃ | Q-1 | — | CO |
| 3-Cl, 5-Cl | CF₃ | CH₂C(O)NHCH₂CN | H | T-3 | CH₃ | Q-1 | — | CO |
| 3-CF₃, 5-CF₃ | CF₃ | CH₂C(O)NHCH₂CF₃ | H | T-3 | CH₃ | Q-1 | — | CO |
| 3-Cl, 4-Cl, 5-Cl | CF₃ | CH₂C(O)NHCH₂CF₃ | H | T-3 | CH₃ | Q-1 | — | CO |
| 3-Cl, 4-F, 5-Cl | CF₃ | CH₂C(O)NHCH₂CF₃ | H | T-3 | CH₃ | Q-1 | — | CO |
| 3-Cl, 5-Cl | CF₃ | CH₂C(O)NHCH₂CF₃ | H | T-20 | — | Q-1 | — | CO |
| 3-CF₃, 5-CF₃ | CF₃ | CH₂C(O)NHCH₂CF₃ | CH₃ | T-20 | — | Q-1 | — | CO |
| 3-CF₃, 5-CF₃ | CF₃ | CH₂C(O)NHCH₂CF₃ | H | T-20 | — | Q-1 | — | CO |
| 3-CF₃, 5-CF₃ | CF₃ | CH₂C(O)NHCH₂CF₃ | H | T-21 | — | Q-1 | — | CO |
| 3-Cl, 5-Cl | CF₃ | CH₂C(O)NHCH₂CF₃ | H | T-21 | — | Q-1 | — | CO |
| 3-Cl, 5-Cl | CF₃ | CH₂CH₂SCH₃ | H | T-21 | — | Q-1 | — | CO |
| 3-Cl, 4-Cl, 5-Cl | CF₃ | C(O)CH₃ | H | T-22 | F | Q-1 | — | CH₂ |
| 3-Cl, 4-Cl, 5-Cl | CF₃ | C(O)CH(CH₃)₂ | H | T-22 | F | Q-1 | — | CH₂ |
| 3-Cl, 4-Cl, 5-Cl | CF₃ | C(O)-cyclo-propyl | H | T-22 | F | Q-1 | — | CH₂ |
| 3-Cl, 4-F, 5-Cl | CF₃ | C(O)CH₃ | H | T-22 | F | Q-1 | — | CH₂ |
| 3-Cl, 4-Cl, 5-Cl | CF₃ | C(O)CH₂CH₃ | H | T-22 | F | Q-1 | — | CH₂ |
| 3-Cl, 4-F, 5-Cl | CF₃ | C(O)CH₃ | H | T-22 | Cl | Q-1 | — | CH₂ |
| 3-Cl, 5-Cl | CF₃ | CH₂C(O)NHCH₂CF₃ | H | T-1 | CH₃ | Q-1 | — | CO |
| 3-Cl, 5-Cl | CF₃ | R³-1 (Z) | H | T-1 | CH₃ | Q-1 | — | CO |
| 3-Cl, 5-Cl | CF₃ | R³-1 (E) | H | T-1 | CH₃ | Q-1 | — | CO |

In an embodiment an isoxazoline for use in the invention is the compound:

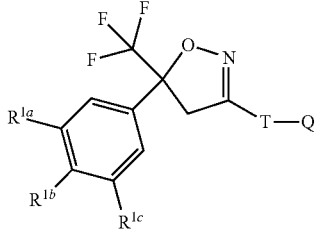

(Formula 2)

wherein $R^{1a}$, $R^{1b}$, $R^{1c}$ are independently from each other: hydrogen, Cl or $CF_3$.

Preferably $R^{1a}$ and $R^{1c}$ are Cl or $CF_3$, and $R^{1b}$ is hydrogen, T is

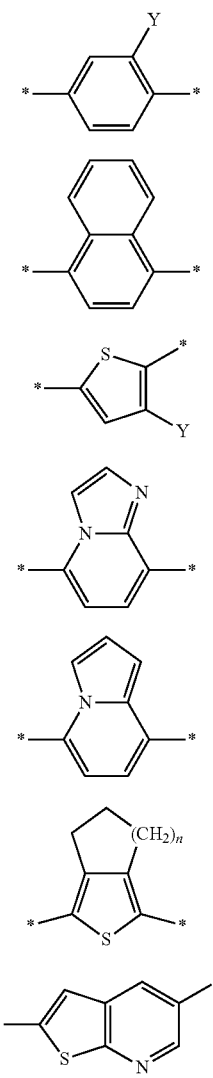

wherein Y is methyl, bromine, Cl, F, CN or $C(S)NH_2$; n=1 or 2; and Q is as described above.

In an embodiment of an isoxazoline as defined herein, $R^3$ is H, and $R^4$ is: —$CH_2$—C(O)—NH—$CH_2$—$CF_3$, —$CH_2$—C(O)—NH—$CH_2$—$CH_3$, —$CH_2$—$CH_2$—$CF_3$ or —$CH_2$—$CF_3$.

In a preferred embodiment of the pharmaceutical composition according to the invention, the isoxazoline is one or more selected from the group consisting of:
Fluralaner,
Afoxolaner,
Lotilaner,
Sarolaner,
(Z)-4-[5-(3,5-Dichlorophenyl)-5-trifluoromethyl-4,5-dihydroisoxazol-3-yl]-N-[(methoxyimino)methyl]-2-methylbenzamide (CAS RN: 928789-76-8),
4-[5-(3,5-dichlorophenyl)-5-(trifluoromethyl)-4H-isoxazol-3-yl]-2-methyl-N-(thietan-3-yl)benzamide (CAS RN: 1164267-94-0), which was disclosed in WO 2009/0080250, and
5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN: 1231754-09-8), which was disclosed in WO 2010/070068.

Isoxazolines can be detected and quantified by liquid chromatography, using standard equipment and procedures.

Therefore, in a preferred embodiment of the pharmaceutical composition according to the invention, the isoxazoline is one or more selected from the group consisting of: Fluralaner, Afoxolaner, Lotilaner, and Sarolaner.

In an embodiment of the pharmaceutical composition according to the invention the isoxazoline is Afoxolaner.

In an embodiment of the pharmaceutical composition according to the invention the isoxazoline is Lotilaner.

In an embodiment of the pharmaceutical composition according to the invention the isoxazoline is Sarolaner.

In an embodiment of the pharmaceutical composition according to the invention the isoxazoline is (Z)-4-[5-(3,5-Dichlorophenyl)-5-trifluoromethyl-4,5-dihydroisoxazol-3-yl]-N-[(methoxyimino)methyl]-2-methylbenzamide (CAS RN: 928789-76-8).

In an embodiment of the pharmaceutical composition according to the invention the isoxazoline is 4-[5-(3,5-dichlorophenyl)-5-(trifluoromethyl)-4H-isoxazol-3-yl]-2-methyl-N-(thietan-3-yl)benzamide (CAS RN: 1164267-94-0), which was disclosed in WO 2009/0080250.

In an embodiment of the pharmaceutical composition according to the invention the isoxazoline is 5-[5-(3,5-Dichlorophenyl)-4,5-dihydro-5-(trifluoromethyl)-3-isoxazolyl]-3-methyl-N-[2-oxo-2-[(2,2,2-trifluoroethyl)amino]ethyl]-2-thiophenecarboxamide (CAS RN: 1231754-09-8), which was disclosed in WO 2010/070068.

In a more preferred embodiment of the pharmaceutical composition according to the invention the isoxazoline is Fluralaner. This showed exceptional efficacy and duration of paraciticidal effect.

The isoxazoline for use in the invention is present in the pharmaceutical composition according to the invention in an amount that is pharmaceutically effective when administered orally by way of medicated drinking water. What is 'pharmaceutically effective' depends of course on a large number of parameters, amongst others on the type of animal and the type of parasite infestation that are being treated. Details are described hereinafter.

For use in the invention, the isoxazoline compound is present in the pharmaceutical composition according to the invention in an amount of between about 0.1 and about 10% w/w of the final pharmaceutical composition according to the invention. Preferably the isoxazoline is present in an amount of between about 0.2 and about 7% w/w; 0.3 and 5% w/w; 0.5 and 3% w/w; 0.6 and 2% w/w, 0.7 and 1.5% w/w; or even between about 0.8 and about 1.1% w/w of the final pharmaceutical composition according to the invention, in that order of preference.

Most preferred amount of isoxazoline in the pharmaceutical composition according to the invention is about 0.95% w/w of the final pharmaceutical composition according to the invention.

For the pharmaceutical composition according to the invention, an amount of isoxazoline of about 0.95% w/w corresponds to a concentration of about 1% w/v.

In a preferred embodiment, the pharmaceutical composition according to the invention comprises: about 9.5 mg of an isoxazoline, alpha-tocopherol at about 66 or at about 82 mg, about 227 mg of Transcutol, and about 681 mg of Tween 80, all per gram of the final pharmaceutical composition according to the invention. In a more preferred embodiment, the isoxazoline is Fluralaner.

As will be self-evident to a skilled person, the pharmaceutical composition according to the invention can induce the effective killing of many parasite species in different types of host animals, by administration via drinking water. Therefore, the precise composition of the pharmaceutical composition according to the invention will depend on the intended use of its dilution in drinking water. Consequently, when used for different animals, the dilution or constitution of the pharmaceutical composition according to the invention can be adapted accordingly. It is well within the routine capabilities of the skilled artisan to adapt, and optimise the details of the pharmaceutical composition according to the invention to such other intended uses, both in regard to the constituents, as well as to their relative amounts.

The pharmaceutical composition according to the invention can be prepared using routine methods and procedures; no special measures need to be taken, as long as the method allows for the complete dissolution of the isoxazoline, and of the complete mixing of all constituents. For example: the isoxazoline is dissolved into the solvent, next the co-solvent is added, and the vitamin E last as this is quite viscous. Alternatively the isoxazoline may be dissolved in a mixture of solvent and co-solvent, after which the vitamin E is added. Dissolution and mixing can occur using standard equipment suitable for industrial-size pharmaceutical preparation. While production will be under controlled and very clean conditions, sterility is not required for a concentrate for mixing with drinking water. The final product is then packaged in suitable containers, which may be of different size, depending on intended scale of use. The product is then stored at room temperature, and no special storage conditions are required. Release testing for quality, quantity and constitution comprises among others: visual inspection for particles, liquid chromatography testing of the level of isoxazoline and vitamin E, and bioburden testing, all according to standard regulations.

Finally the commercial product: the pharmaceutical composition that is a concentrated solution, for dilution in drinking water, is released for sale.

General techniques and considerations that apply to the preparation of pharmaceutical composition are well-known in the art and are described for instance in governmental regulations (Pharmacopoeia) and in handbooks such as "Remington" (supra).

Therefore, in a further aspect the invention relates to a method for the preparation of the pharmaceutical composition according to the invention, the method comprising the steps of dissolving the isoxazoline and mixing the vitamin E in a pharmaceutically acceptable solvent.

The method for the preparation of the pharmaceutical composition according to the invention, can in principle be performed using standard materials and methods. There are only a few preferred conditions:

Preferably the isoxazoline is added to the solvent (and optionally the other liquids), not the other way around. This assists in the complete dissolution of the isoxazoline;

Preferably the temperature of the composition in preparation should remain at about room temperature, and preferably not exceed 40° C., and particularly not exceed 60° C. This because vitamin E is temperature sensitive; and The composition is mixed for as long as is needed to achieve complete dissolution and mixing of all ingredients.

As described herein, an isoxazoline parasiticide can conveniently be administered by oral administration to animals, via the animal's drinking water. This way a medicated drinking water is used for the treatment or prevention of parasite infestation of animals. To accommodate for variations in the quality or the composition of the drinking water, a vitamin E is advantageously present, and prevents degradation of the isoxazoline active compound when diluted in the drinking water.

Therefore, in a further aspect the invention relates to a medicated drinking water comprising a dilution in drinking water of the pharmaceutical composition according to the invention, or of a pharmaceutical composition as obtainable by the method for the preparation of the pharmaceutical composition according to the invention.

The medicated drinking water according to the invention will then contain the constituents of the pharmaceutical composition according to the invention, in an amount that corresponds inversely to the level of dilution that was applied to the pharmaceutical composition in the drinking water.

The level of dilution of the pharmaceutical composition according to the invention can be selected on the basis of the desired therapeutic dose of isoxazoline that a group of animals needs to be administered, in relation to their average weight and the expected volume of the medicated drinking water that the group is expected to drink over a number of hours.

For example: if a laying hen of about 1 kg bodyweight is to be treated with a therapeutic concentration of an isoxazoline of about 0.5 mg/kg, she should ingest a total of about 500 µg isoxazoline. When a treatment period of about 4 hours is selected, the hen can consume about 50 ml of medicated drinking water; therefore the medicated drinking water should contain about 10 µg/ml of active.

More examples of dosing calculations are presented in the Examples section.

Similar calculations can be made for other therapeutic doses, or for other animals such as swine or bovines, after which the duration of exposure and the total amount of isoxazoline in the medicated drinking water can be determined, based on the (estimated) total number of animals that is to be treated, and their average weight.

As the skilled person will understand from this non-binding example, characteristic for the veterinary administration of a pharmaceutical by a method of mass administration, especially when the number of animals to be treated is very large, is that several of the parameters for the treatment of the animals must be based on assumptions and average values. Therefore, while several of these parameters are known in the art, animal caretakers or veterinarians may factor-in certain safety margins, e.g. in respect of duration of treatment or volume of the medicated drinking water to be administered, based on their experience. Certain parameters can be measured, to assist in the determination of relevant parameters: e.g. drinking water consumption can be monitored by reading a water meter over a certain period of time, and factor-in effects of weather and temperature at the moment of treating the animals. Similarly, average body weight can be determined by measuring bodyweight from a representative number of animals shortly before administration.

In an embodiment, the medicated drinking water according to the invention is a dilution of the pharmaceutical composition according to the invention in drinking water of between about 1:10 and about 1:100.000.

In a further embodiment the medicated drinking water according to the invention is a dilution of the pharmaceutical composition according to the invention in drinking water of between about 1:50 and about 1:50.000; 1:100-1:10.000; 1:200-1:5000, or even between about 1:250 and about 1:2500.

In a preferred embodiment the medicated drinking water according to the invention comprises dissolved isoxazoline at between about 0.1 and about 50 µg/ml, preferably at about 0.5 and about 25 µg/ml.

Because the pharmaceutical composition according to the invention allows for its full and complete dispersion in drinking water, therefore a mere dilution of the pharmaceutical composition in drinking water, will not change significantly the ratio of the amounts of the constituents of the pharmaceutical composition towards each other.

Therefore in an embodiment of the medicated drinking water according to the invention, the ratio's of the amounts of the isoxazoline, solvent, additional solvent and vitamin E towards each other is the same as in the pharmaceutical composition according to the invention.

In an embodiment, the medicated drinking water according to the invention comprises: between about 0.0008 and about 0.0011% of an isoxazoline; between about 0.005 and about 0.009% of a vitamin E; between about 0.02 and about 0.025% of an ethoxy-ethanol; and between about 0.06 and about 0.075% of a polysorbate, all in % w/w of the medicated drinking water.

In a preferred embodiment, the medicated drinking water according to the invention comprises about 9.5 µg of an isoxazoline, alpha-tocopherol at about 66 µg or at about 82 µg, about 227 µg of Transcutol, and about 681 µg of Tween 80, all per gram of the medicated drinking water. More preferably, the isoxazoline is Fluralaner.

As the skilled person will understand, the exact amount of the constituents in the medicated drinking water according to the invention may not be apparent from testing a single sample of a medicated drinking water. This is because its composition may show some variation over time, and is dependent from the point of sampling, e.g. the distance from the point where the medicated drinking water enters the drinking water installation, and of the amount of unmedicated drinking water that was in the system when the medicated drinking water was administered.

Consequently, for use in the invention the composition of the medicated drinking water described herein, refers to the composition as measured at a point at between about 1 and about 5 meters downstream of the point where the medicated drinking water enters the drinking water installation, and by analysing and averaging the measurements of at least 5 samples, taken intermittently over a period of about 15 minutes. This way of sampling serves to even out variations in composition caused by hydro-mechanical characteristics of the drinking water system that is being monitored.

Preferred method for detecting isoxazoline or vitamin E in a sample of medicated water, is by liquid chromatography technique.

As is described below, there are several ways in which the medicated drinking water according to the invention can be prepared and can be fed into the drinking water installation.

The medicated drinking water according to the invention is most advantageous when prepared from drinking water that contains a water sanitizer. In such drinking water, the isoxazoline would normally become degradated and loose its pharmaceutical efficacy. However by the incorporation of a vitamin E such degradation is prevented.

Therefore in an embodiment, the medicated drinking water according to the invention comprises a water sanitizer.

For use in the invention, 'comprises a water sanitizer' covers the situation where the drinking water with which the medicated drinking water according to the invention is to be prepared, contains or has previously contained, a water sanitizer. As the skilled person will appreciate, whether a water sanitizer is actually present at a certain point in time, and in a particular test sample of drinking water, and if so in what amount, depends on a number of parameters. For example, the water sanitizer may be sensitive to natural or physical influences such as UV light, pH or temperature, and so become degradated over time. Also the level of water sanitizer may be different for samples taken at different sampling points in the drinking water installation. Also, the volume amount of water sanitizer present in the medicated drinking water may gradually decrease because of its interaction with the diluted pharmaceutical composition according to the invention; in particular because of an interaction with the vitamin E.

Therefore, to determine for use in the invention the level of water sanitizer in a drinking water, this should be measured at a point at between about 1 and about 5 meters downstream of the point where the sanitised water enters the drinking water installation, and by analysing and averaging the measurements of at least 5 samples, taken intermittently over a period of about 15 minutes.

Therefore in an embodiment, a medicated drinking water according to the invention, preferably contains, or has contained at some point in time, a water sanitizer in an amount of at least about 0.1 ppm. Preferably a medicated drinking water according to the invention, contains, or has contained, a water sanitizer in an amount of at least about 0.25 ppm, 0.5, 0.75, 0.9, 1, 1.25, 1.5, 2, 2.5, 3, 3.5, 4, 5, 6, 7, 8, 9, or even at least about 10 ppm of a water sanitizer, in this order of preference.

NB: For hypochlorite 1 ppm in water equals $2 \times 10^{-5}$ moles hypochlorite per litre.

For use in the invention, the amount of a water sanitizer in drinking water can be determined by any suitable technique, e.g. by a method of chemical titration.

A 'water sanitizer' for use in the invention is a compound that can provide for some way of disinfection of microorganisms that may contaminate the drinking water. Typically such disinfection is obtained by chemical means such as by an oxidising radical, in which case the water sanitizer is called an oxidising sanitizer.

Preferably the oxidising sanitizer contains a chlorine atom, and preferably is hypochlorite or chlorine dioxide. Such water sanitizers are well-known in the field and are generally available.

Therefore, in an embodiment the water sanitizer in the medicated drinking water according to the invention is an oxidizing sanitizer; preferably the oxidizing sanitizer for use in the invention contains a chlorine atom; more preferably the oxidizing sanitizer is hypochlorite or chlorine dioxide.

Although not required for pharmaceutical efficacy, the medicated drinking water according to the invention may comprise one or more additional pharmaceutically acceptable constituents, for reasons such as convenience, stability, or efficacy. Of course such an additional constituent should not interfere with the efficacy of the isoxazoline treatment. The additional constituent may be added at any convenient point in time, for instance upon the preparation of the medicated drinking water, or later, after the medicated drinking water was prepared. The additional constituent is preferably incorporated into the pharmaceutical composition according to the invention.

In an embodiment, an additional constituent for the medicated drinking water according to the invention is a pharmaceutically acceptable colouring agent, such as a dye or pigment. This will allow visual monitoring of the actual uptake by the animals of the medicated drinking water, by detecting the colouring agent's colour in their mouth or on the tongue. Such a colouring agent should of course be allowed for oral administration to food animals, and should readily dissolve in drinking water. Suitable colouring agents are those allowed under the US Federal Food, Drug, and Cosmetic Act (FD&C) such as FD&C Blue n° 1, or natural food dyes such as Chlorophyllin (green), or Carmine (red).

The medicated drinking water according to the invention can conveniently be prepared by dissolving into drinking water the pharmaceutical composition according to the invention.

Therefore, in a further aspect the invention relates to a method for the preparation of the medicated drinking water according to the invention, the method comprising the step of diluting into drinking water the pharmaceutical composition according to the invention, or a pharmaceutical composition as obtainable by the method for the preparation of the pharmaceutical composition according to the invention.

In an embodiment of the method for the preparation of the medicated drinking water according to the invention, the dilution of the pharmaceutical composition according to the invention in drinking water is a dilution of between about 1:250 and about 1:2500.

In large scale animal farming operations, complex water installations are common, using a high or low pressure ring system for drinking water distribution, with dead end- or closed loop systems, of different lengths, and with different pipe materials (e.g. PVC or galvanized iron), and with drinkers which are adapted to the target animals such as bell drinkers, nipples, etc. These installations may be provided with systems to prepare and provide sanitised drinking water to the animals. Commonly also systems are used for orally administering medicaments and/or vaccines to the animals via the drinking water.

The main systems for providing water medication are a separate medication tank with a (pre-) dilution of the pharmaceutical compound, or a dosing system. The medication tank may be used to add to the main water lines, in which case the medication tank will contain a pre-dilution of the active, that will become further diluted to its final desired dilution, upon mixing with the main water lines; alternatively the medication tank may already contain the active in the desired final dilution, and will then be used to completely replace the regular drinking water stream for a certain period.

Alternatively, medicated drinking water can be prepared by using a device for dosing or proportioning, such as a dosing pump that is electronic (Konti-Dos™, Burkert), or mechanical (from Dosatron, USA, or from HydroSystems, USA), to inject measured amounts of a more or less concentrated solution of an active pharmaceutical compound directly into the drinking water installation. Here the medicated water in its final dilution also forms by the mixing into the main water stream. Depending on the dilution level that a dosing pump can reach, the pump must be fed with a more or less concentrated solution of the active. For example if the dosing pump can reach a dilution range of 5%, which is 1:20, and the desired final dilution of the pharmaceutical composition in the medicated drinking water is e.g. 1:1000, then the dosing pump needs to be fed with a pre-dilution at 1:50 of the pharmaceutical composition in drinking water.

Exemplary calculations on preparation of medicated drinking water according to the invention using either a dosing pump or a medication tank are provided in the Examples section.

Either way, the medicated drinking water is produced by diluting and mixing a volume of a pharmaceutical composition according to the invention with drinking water until a sufficient amount of the active compound is comprised in a desired volume of drinking water, in a sufficient volume of drinking water that will be consumed by the number of animals to be treated, during a certain treatment period, so as to provide on average each animal with a therapeutically effective dose of the active.

To assure that all animals will consume the medicated drinking water, and thus a dose of the active compound, the animals can be left to thirst for a short while before the administration of medicated drinking water, by temporarily cutting off the water supply. Also, the volume of the medicated drinking water to be prepared can be set at a volume that is less than what the animals would on average consume in a certain period of time, for example at 75 or 50% of that volume. This can help to achieve the complete consumption of the volume of medicated water provided. After this complete consumption, the flow of regular drinking water is resumed.

Preferably the drinking water installation is flushed with water prior to the administration of medicated drinking water, to rinse the installation, and to remove any traces of previous treatments. Next the installation is preferably drained, so that the medicated water provided next is not unintentionally diluted.

When transporting the medicated drinking water according to the invention through PVC- or PE tubes, no significant sorption was detected of the isoxazoline to the tubes. Also no significant foaming was observed. Further the medicated drinking water did not clog or block any of the pipes or the drinking nipples. But rather, after the treatment was terminated and regular drinking water supply was resumed, the level of isoxazoline in the drinking water was rapidly reduced, and was down to undetectable levels within one hour.

Therefore in an embodiment of the method for the preparation of the medicated drinking water according to the invention, the pharmaceutical composition according to the invention, or a pharmaceutical composition as obtainable by the method for the preparation of the pharmaceutical composition according to the invention, is diluted by admixing through a dosing pump system in a water system, or by admixing with drinking water from a medication tank.

The preparation of any pre-dilution of the pharmaceutical composition according to the invention, in preparation for making the medicated drinking water, is well within the routine capabilities of the skilled artisan, and is therefore comprised within the scope of the methods and uses for the invention.

Especially advantageous results are obtained when the drinking water that is used for the preparation of the medicated drinking water according to the invention, contains a water sanitizer.

Therefore in an embodiment of the method for the preparation of the medicated drinking water according to the invention, the drinking water comprises a water sanitizer.

In a further embodiment of the method for the preparation of the medicated drinking water according to the invention, the water sanitizer in the drinking water is an oxidizing sanitizer; preferably the oxidizing sanitizer for use in the invention contains a chlorine atom; more preferably the oxidizing sanitizer is hypochlorite or chlorine dioxide.

This way of preparation of a medicated drinking water according to the invention represent an advantageous medical use of the pharmaceutical composition according to the invention.

Therefore, in a further aspect the invention relates to the use of the pharmaceutical composition according to the invention, or of a pharmaceutical composition as obtainable by the method for the preparation of the pharmaceutical composition according to the invention, for the preparation of the medicated drinking water according to the invention, by diluting the pharmaceutical composition in sanitized drinking water.

The compositions, dilutions, methods and uses according to the invention, as described above, allow for a variety of ways for the prophylaxis (prevention) and/or the therapy (treatment) of parasitic infestations of animals. This way parasite infestations can be effectively removed or reduced, and/or can be prevented from expanding or even from occurring altogether.

Therefore, in a further aspect the invention relates to the pharmaceutical composition according to the invention, or to a pharmaceutical composition as obtainable by the method for the preparation of the pharmaceutical composition according to the invention, for use in the treatment or prevention of parasite infestation of animals.

Also, in a further aspect the invention relates to the use of the pharmaceutical composition according to the invention, or of a pharmaceutical composition as obtainable by the method for the preparation of the pharmaceutical composition according to the invention, for the manufacture of a medicament for the treatment or prevention of parasite infestation of animals.

The 'treatment', and similar terms such as 'treating' or 'treat' as used herein, refer to the administration of an effective amount of an isoxazoline as described for use in the invention to an animal which has an infestation—of more or less severity—with parasites of one or more species.

What constitutes an 'effective amount' for use in the invention, is the amount, therapeutic dose, or quantity of an isoxazoline as described herein, that is required for the complete eradication of the parasites infesting such animal, or for at least a significant reduction of the parasites infesting an animal. Alternatively, this may refer to an amount, dose, or quantity that can effectively control and/or reduce presence of parasites in an animal's housing or its surroundings, e.g. the house, building, farm, fields, etc.

To establish that an effective reduction of infestation of an animal, or an effective control and/or reduction of parasites in the surroundings has occurred, and thus: what constitutes such an effective amount, is readily determined by comparing the parasite numbers either on the animal or in an animal's environment, before and after administering an isoxazoline as described herein. Detection can be done by counting of the number of parasites visible on an animal, or by counting parasites using a trap or other detection-device in the surroundings. The difference in numbers from such counts made before and after treatment indicates the efficacy of the dose applied. To make such counts statistically reliable, a certain minimal number of host animals or detection devices will need to be monitored.

Alternatively the effect on the economic performance of the animals can be monitored, such as for example a difference in: daily weight gain, feed conversion, or the production of milk or eggs.

So, although reductions at—or close to 100% are aimed for, however a reduction in parasite numbers of about 5% may already constitute a significant reduction. This because even such a modest reduction already alleviates certain symptoms for affected animals, and may restore the animals to an improved economic production level.

In a preferred embodiment, the reduction of infestation on an animal, or the control and/or reduction achieved, regards a reduction in the number of a particular type of parasite by at least 5, 10, 15, 20, 25, 30, 40, 50, 60, 70, 75, 80, 85, 90, 91, 92, 93, 94, 95, 96, 97, 98, 99, or even 100%, in that order of preference.

Similarly, 'prevention' or 'prophylaxis' means that a new infestation of the animal with parasites is prevented by killing adult parasites and any developmental or larval stage that is able to infest the host, before infestation of the host or directly after infestation of the protected host, and/or to prevent or reduce the development of new generations of parasites, in whole or in part.

The effect of the treatment or prevention for use in the invention with an isoxazoline as described herein on a parasite, can e.g. be ovicidal, larvicidal and/or adulticidal or a combination thereof. The effect can manifest itself directly, i.e. killing the parasites either immediately or after some time has elapsed, for example when molting occurs, or by influencing the duration or the number of bites, or the amount of blood or body fluid ingested by the parasite per bite. Alternatively the effect may be on the number of offspring from the parasites, directly or in subsequent generations, e.g. by reducing the parasites' fertility or oviposition efficiency, such as the size, number or quality of eggs laid; the hatching rate; the viability of the outcome; or the gender ratio of the outcome.

For use in the invention a 'parasite' is any noxious organism that negatively affects the health, well-being, or economic production level of a host animal. Parasites can be endo- or ectoparasites, and may be attached in or on a host animal, and in a temporary or a stationary manner.

In one embodiment the parasite infestation that is prevented or treated is an ectoparasite infestation.

Specific examples of ectoparasites include, but are not limited to, fleas (*Ctenocephalides* sp., e.g. *C. felis*), ticks (*Rhipicephalus* sp., *Ixodes* sp., *Dermacentor* sp., *Amblyomma* sp., *Haemaphysalis* sp., *Boophilus* sp.), and mites (*Demodex* sp., *Sarcoptes* sp., *Otodectes* sp., *Cheyletiella* sp., *Psoroptes* sp., *Chorioptes* sp., *Dermanyssus* sp., *Ornithonyssus* sp.), lice (*Bovicola* sp., *Trichodectes* sp., *Felicola* sp., *Linognathus* sp.), mosquitoes (*Aedes* sp., *Culex* sp., *Anopheles* sp.) and flies (*Hematobia* sp. e.g. *H. irritans, Musca* sp., *Stomoxys* sp. e.g. *S. calcitrans, Dermatobia* sp., *Cochliomyia* sp.).

As the skilled person will appreciate, the infestation of an animal or its housing or its surroundings, may be made up of one or more species, types, or genera of parasites.

In an embodiment, the parasite infestation relates to an infestation of poultry, or a poultry house or -farm. Therefore, for use in the invention, preferred parasites are one, more, or all of:

mites: poultry red mite (*Dermanyssus gallinae*), Northern fowl mite (*Ornithonyssus sylviarum*), scaly leg mite (*Knemidokoptes mutans*), tropical fowl mite (*Ornithonyssus bursa*), follicle mites (*Demodex folliculorum*), and itch- or scabies mites (*Sarcoptes* sp., *Cheyletiella* sp., *Psorioptes* sp.);

ticks: fowl ticks (*Argas persicus*);

lice: chicken body louse (*Menacanthus stramineus*), and shaft louse (*Menopon gallinae*);

bugs: common bedbug (*Cimex lectularius*), and poultry bug (*Haematosiphon inodora*); and fleas: sticktight flea (*Echidnophaga gallinacea*), and hen flea (*Ceratophyllus gallinae*).

Therefore in an embodiment the invention relates to the pharmaceutical composition according to the invention, or to a pharmaceutical composition as obtainable by the method for the preparation of the pharmaceutical composition according to the invention, for use in the treatment or prevention of infestation of birds with mites, ticks lice, bugs, or fleas.

In an embodiment the invention relates to the use of the pharmaceutical composition according to the invention, or of a pharmaceutical composition as obtainable by the method for the preparation of the pharmaceutical composition according to the invention, for the manufacture of a medicament for treatment or prevention of infestation of birds with mites, ticks lice, bugs, or fleas.

More preferred parasites are mites; even more preferred are poultry red mites or Northern fowl mites.

For use in the invention, 'animals' are non-human animals. Also the animals are of relevance to veterinary science and/or are of economic relevance in commercial animal husbandry. In an embodiment animals are swine, bovines, goat, sheep, horse, dog, cat, or bird.

Preferred animals are birds, pigs, or bovines.

For use in the invention 'bovines' are taurine cattle (*Bos taurus*), zebu cattle (*Bos indicus*), buffalo, bison, yak, or wisent.

The term "swine" refers to animals of the family of Suidae, and preferably to animals of the genus *Sus*, which are also referred to as porcines. Examples are: a wild or a domestic pig, hog, wild boar, babirusa, or warthog. This also includes swine indicated by an arbitrary name, for example referring to their sex or age such as: sow, queen, boar, barrow, hog, gilt, weaner, or piglet.

For use in the invention 'birds' are avian species of relevance to humans or to the veterinary field, for example: chicken, turkey, duck, goose, partridge, peacock, quail, pigeon, pheasant, guinea fowl, finch, crow, parakeet, parrot, ara, macaw, cockatoo, falcon, hawk, emu, cassowary, or ostrich.

Preferred animals are birds; more preferred birds are selected from the group consisting of: chicken, turkey, duck and goose. Even more preferred is: chicken.

For use in the invention, the birds can be of any type, breed, or variety, such as: layers, breeders, broilers, pullets, combination breeds, and replacement- or parental lines of any such breeds. Preferred types are: broiler, breeder, pullets and layer. More preferred are layer birds.

Layer birds produce eggs that may be of the type for human consumption, or which may be intended for breeding. Because this type of bird commonly sits down at night, these layer birds suffer most from infestation with mite infestation of a poultry house or -farm.

An especially advantageous effect of the compositions and dilutions according to the invention, is that there is no withdrawal period for the use of the eggs of treated birds, so that the treatment can be applied during the active egg production period. This is because the dose of isoxazoline that is required for high effectivity against certain parasites in the birds, especially against mites, by oral uptake is very low. This way the residue levels in eggs remains far below the MRL value of Fluralaner, so that eggs remain safe for human consumption, and no discharge of eggs is required. Withdrawal time for meat and offal is about 7 days.

Similarly, the dose of Vitamin E used in the sanitized drinking water is so low that it is far below the ADI for human consumption, so that eggs remain safe for consumption even during an anti-parasite treatment according to the invention.

Most preferred layer birds are layer chickens.

Animals for the treatment or prevention for use in the invention can in principle be of any age, weight, sex, or immunological status, although it is evidently favourable to treat the animals as healthy and as early as possible.

Because a parasite infestation can in principle occur at any age of the animals, therefore the treatment for use in the invention is preferably applied from as young as 1 day of age; preferably from about 1 week of age. More preferably, chickens are treated from about 3 weeks of age.

While the treatment or prevention for use in the invention can be administered regularly, or incidentally when appropriate; such a treatment is preferably integrated into an existing schedule of treatments of the animals with other pharmaceutical- or biological preparations. Such integration may reduce handling-related stress to the animals and reduce labour costs. These other preparations can be administered in a simultaneous, concurrent or sequential fashion with a treatment for use in the invention, in a manner compatible with their registered use, and a manner which does not interfere with an effective prevention or treatment of a parasite infestation for use in the invention.

One other favourable effect of a treatment for use in the invention is that when an animal no longer suffers from (serious) parasite infestation, its general health will improve, so that it will also be better able to resist other diseases or plagues, or it may respond better to other treatments. All this contributes to an increase of the animal's well-being and its economic performance.

The treatment or prevention for use in the invention is by oral administration to animals via their drinking water. This is a type of systemic administration that involves uptake of the active compound via the enteric route, after which the active is distributed to tissues and fluids all over the animal's body. This way a parasite will ingest a lethal dose of the active by feeding on the host animal in principle at any place in- or on the body.

Because the compound is very active at a very low dose, onset of action is very quick, and mites start dying immediate after their blood meal. Also the duration of 100% killing was found to continue at 7 and at 15 days. Even parasites resistant to standard antiparasiticides, showed high sensitivity to isoxazolines.

The oral administration by drinking water route is applied by providing animals with medicated drinking water according to the invention.

Therefore, in a further aspect the invention relates to a method for the treatment or prevention of parasite infestation of animals, comprising the administration to the animals of the pharmaceutical composition according to the invention, or to a pharmaceutical composition as obtainable by the method for the preparation of the pharmaceutical composition according to the invention, via medicated drinking water.

And subsequently, a further aspect of the invention relates to the medicated drinking water according to the invention or to a medicated drinking water as obtainable by the method for the preparation of the medicated drinking water according to the invention, for use in the treatment or prevention of parasite infestation of animals.

A medicated drinking water according to the invention can in principle be prepared at any level of dilution of the pharmaceutical composition according to the invention, between the undiluted pharmaceutical composition and the final dilution that is to be administered to animals. Such medicated drinking waters of intermediate dilution can serve as pre-dilutions, or stock solutions, that can be used to prepare subsequent dilutions steps. Examples are the intermediate dilutions to be used with a dosing pump or a medication tank. Consequently, a medicated drinking water according to the invention can itself be used to prepare a (further) medicated drinking water for administration to animals.

Therefore, in a further aspect the invention relates to a medicated drinking water according to the invention or to a medicated drinking water as obtainable by the method for the preparation of the medicated drinking water according to the invention, for the manufacture of a medicament for the treatment or prevention of parasite infestation of animals.

In a further aspect the invention relates to a method for the treatment or prevention of parasite infestation of animals, comprising the administration to the animals of the medicated drinking water according to the invention or to a medicated drinking water as obtainable by the method for the preparation of the medicated drinking water according to the invention.

Very advantageous to the methods of treatment and prevention according to the invention, is that these can be simply be applied during an ongoing production cycle, because no special preparations are required. For instance no clearing of the house from feed, animals, bedding, or product such as eggs is needed, saving much time and effort, as well as potential stress to the animals. Also animals in any stage of production, or reproduction can be treated.

The methods of treatment according to the invention, regard the oral administration to animals of an isoxazoline as described for use in the invention, via their drinking water, either by administering (a dilution of) a pharmaceutical composition according to the invention, or of a medicated drinking water according to the invention.

In all cases these methods of treatment are targeted to animals in need of such treatment, which in practice are all types of animals susceptible to a type of ectoparasite. Also the treatment regards the administration of a pharmaceutical effective dose (the amount) of the isoxazoline to be administered. The level of this dose depends on a number of parameters, such as the type and weight of the animal. In general the pharmaceutically effective amount per kg bodyweight of the animals treated is dictated by the type and the severity of the parasite infestation being treated and is known in the art.

In an embodiment, the method for treatment according to the invention, regards the administration via drinking water to an animal of an isoxazoline as described herein at an amount of between about 0.01 and about 100 mg/kg bodyweight. Preferred amount is between about 0.05 and about 50 mg/kg, 0.1-25, 0.2-10, 0.25-5, and even between about 0.5 and about 2.5 mg/kg bodyweight, in this order of preference.

In an embodiment the amount of the isoxazoline as described herein to a chicken is between about 0.1 and about 1 mg/kg bodyweight, preferably between about 0.5 and about 1 mg/kg bodyweight. Preferred isoxazoline for use in the invention is Fluralaner.

The animal's 'bodyweight' is determined as its live bodyweight. As this will change over time, and likely increase as the animal grows, a treatment at a later time may require the amount of active administered to be adapted, c.q. increased. This can conveniently be obtained by increasing the concentration of the active in the medicated drinking water (e.g. by reducing the level of dilution of the pharmaceutical composition), or by increasing the volume of medicated drinking water provided (e.g. by increasing the period that medicated drinking water is provided to the animals).

The treatment for use in the invention can be made available during a treatment period to a single animal. More advantageous is the treatment at the same time of a group of animals, or to all animals in a single stable, house, or farm via the medicated drinking water according to the invention.

A convenient period for treatment using the medicated drinking water according to the invention, is for a period between 1 and 24 hours, preferably between 2 and 20, or 3-12 hours, more preferably between about 4 and about 8 hours, so that the treatment can be finished during a single working day, or during an average work-shift of a team of personnel.

During a treatment period, all animals should have unrestricted access to the medicated drinking water, and preferably the total volume of the medicated drinking water offered should be consumed; after complete consumption, access to unmedicated drinking water should be restored.

In an embodiment, the treatment for use in the invention by oral administration via medicated drinking water to poultry, is preferably applied to animals that are kept for breeding or egg laying, and consequently are kept in one house longer than approximately 8 weeks. Especially preferred is the administration to laying hens.

This is because parasite infestations may develop over a period of time; for example a mite population will only start to develop when a poultry house is populated, and will then rapidly expand, for several weeks until they become a real nuisance to the animals.

The frequency of the treatment for use in the invention, depends on the type and severity of the parasite infestation treated or prevented, as well as on the production cycle of the host animal treated.

For some parasites, not all stages of the parasite can be reached by a single treatment via administration of medicated drinking water, because specific parasite stages do not (yet) feed on the animal. With the administration of a second dose of an isoxazoline via medicated drinking water, the parasites can be reached, that developed (following the lifecycle of the parasites) from not susceptible, or difficult to reach parasite stages, e.g. that matured from the juvenile stages of the parasites (such as eggs, nymphs or pupae) during this period.

Therefore in an embodiment, the treatment according to the invention is applied via the administration of medicated drinking water, at least once, or twice per production cycle of the host animal treated.

In a preferred embodiment, when the animal is a layer bird, the production cycle for use in the invention regards one whole laying period; in case of layer chickens this is about 25 weeks.

In a preferred embodiment of the method for treatment according to the invention, the treatment is given in two stages, about 3 days to about 14 days apart. This is conveniently selected depending on the parasite lifecycle, and on the production cycle of the host animal.

More preferred is a treatment of layer chickens, twice, 7 days apart. Even more preferred is a treatment where the isoxazoline is Fluralaner; even more preferred is when the amount applied is 0.5 mg/kg bodyweight per treatment.

Preferably, the medicated drinking water is prepared fresh for each of the treatments.

By this administration regimen of administration several days apart a longer duration of efficacy against the parasitic arthropods can be achieved, because different lifecycle stages of the parasites can be reached by such timed administration. The specific time interval can be different for the various parasitic arthropods and can be depending on the environmental conditions that influence the parasite lifecycle. With the administration of a second dose the parasites can be reached that developed (following the lifecycle of the parasites) from not susceptible, or difficult to reach parasite stages, e.g. that matured from the juvenile stages of the parasites (such as eggs, nymphs or pupae) during this period.

By such administration regimen the parasite population can be significantly reduced to a level that would only cause minimal damage to the animal and minimal production losses during this production cycle, or even more than one production cycle. One specific benefit of such administration regimen is that a low dosage of the isoxazoline compound can be administered so that residues in eggs can be minimized by such administration regimen while maintaining effective control of parasitic arthropods.

In an embodiment, the invention regards a method of treating or preventing poultry red mites or Northern fowl mites on poultry in need of such treatment, by oral administration to these poultry a pharmaceutical effective dose of an isoxazoline as described for use in the invention, via their drinking water. The preferred isoxazoline is Fluralaner; the preferred poultry are chickens, in particular laying hens.

Such an effective treatment schedule will also be effective in controlling and/or reducing the presence of parasites in the animal's surroundings, such as the house, building, farm, or fields.

Therefore in a further aspect the invention relates to a method for controlling and/or reducing parasitic arthropods in animal surroundings, the method comprising the administration to the animals of the medicated drinking water according to the invention, or of a medicated drinking water as obtainable by the method for the preparation of the medicated drinking water according to the invention.

Advantageously, such a method for controlling and/or reducing parasitic arthropods in animal surroundings, is part of an integrated pest-management program. It is good practice in the field to rotate between types of pest control treatments, in particular to prevent development of resistance in the parasites. However, because an isoxazoline treatment as described herein, is highly effective when applied at the recommended dose, it is not expected to lead to resistance in the ectoparasites. Consequently such methods can be applied over a longer time than other classes of antiparasiticides.

As is evident from the description and from the examples provided hereinafter, the inventors have devised a way to significantly improve the treatment of animals with an isoxazoline by administration via drinking water. This because the incorporation of a vitamin E provides protection to the isoxazoline from degradation in different types of drinking water, especially in drinking water comprising a water sanitizer.

Therefore in a further aspect the invention relates to the use of a vitamin E for the protection of an isoxazoline as described for use in the invention from degradation in medicated drinking water, wherein the drinking water comprises a water sanitizer.

In preferred embodiments one, more or all of these aspects apply:
the isoxazoline is Fluralaner,
the vitamin E is alpha-tocopherol,
the water sanitizer is an oxidizing sanitizer,
the oxidizing sanitizer is hypochlorite or chlorine dioxide.

In practice, the pharmaceutical composition according to the invention can be commercialised as such, packaged in an appropriate container, for use by customers to prepare the medicated drinking water according to the invention.

Therefore, in a further aspect the invention relates to a container comprising the pharmaceutical composition according to the invention, or a pharmaceutical composition as obtainable by the method for the preparation of the pharmaceutical composition according to the invention.

Appropriate containers for use in the invention will have to be practical and resilient to allow convenient storage, transportation, and use. Also they will have to be made of pharmaceutically acceptable material, which will not negatively influence the pharmaceutical effectivity of the active, or the stability upon prolonged storage.

Examples of material for appropriate containers are glass, plastics, or metals. Preferred material is HDPE (high-density polyethylene).

Examples of forms of appropriate containers are flasks, sacks, boxes, jerry cans, and the like. The containers should be enclosed with a lid that is removable such as a tear-off or screw-off lid, or a lid that is pierceable, such as stopper of rubber or plastic.

Container form can be determined by requirements of production, transport and storage, handling, etc. Preferred container form is a rectangular jerry can, with screw-off lid, and optional tear-off seal.

Examples of appropriate size for containers for use in the invention are containers with a volume that allows the treatment of a considerable size group of animals, once or twice, during one animal production cycle. Preferred volumes for a container for use in the invention are between 0.01 and 1000 litres, preferably between 0.1 and 100, more preferably between 0.5 and 10 litres.

In accordance with governmental regulations for veterinary pharmaceutical products, the container according to the invention will be commercialised together with appropriate labelling and instructions, which can conveniently be combined in a kit of parts.

Therefore in a further aspect the invention relates to a kit of parts, the kit comprising a container according to the invention, and instructions for use of the pharmaceutical composition according to the invention, or of a pharmaceutical composition as obtainable by the method for the preparation of the pharmaceutical composition according to the invention.

The instructions comprised with the kit of parts according to the invention, may for example be provided by way of information written on, or attached to, the container or on a box containing the container; may be present on a leaflet packaged with the container, such as a patient information leaflet or a package insert; and/or the instructions may be provided by way of a reference to instructions in electronic form, such as information viewable on, or downloadable from, an Internet website from the distributor of the kit, and the like.

For use in the invention, the kit may also be an offer of the mentioned parts (relating to commercial sale), for example on an internet website, for a use comprising a method according to the invention.

The invention will now be further described by the following, non-limiting, examples.

EXAMPLES

Example 1: Efficacy of Fluralaner in Medicated Drinking Water Against Poultry Red Mite Infestation of Chickens As a comparative example, the results in this Example demonstrate the parasiticidal efficacy of Fluralaner, when administered orally via medicated drinking water, to control an artificially induced infestation of laying hens with poultry red mite (*D. gallinae*). The drinking water used was regular tap water not comprising a significant amount of oxidising sanitizer, and no vitamin E was used in the concentrated Fluralaner solution used.

1.1. Materials and Methods

Experimental animals were chickens, particularly laying hens of about 30 weeks old. These were housed in a standard poultry house. Apparently healthy birds were assigned in a random way to treatment groups kept separately, and labelled individually. The birds were kept under natural light, and were given several days for acclimatization; drinking water consumption in each group was measured on three days prior to administration to calculate the average daily water consumption. Medicated water was prepared by diluting a concentrated Fluralaner solution (10 mg/ml) to the desired concentration of Fluralaner in regular tap water (hypochlorite <0.5 ppm).

The concentrated Fluralaner solution used was comparable to a pharmaceutical composition according to the invention, except that no vitamin E was present, and consisted of: 0.95% w/w Fluralaner, 24.76% w/w Transcutol V, and 74.29% w/w Tween 80.

Groups A-D (n=6) were treated with doses of 2, 1 or 0.5 mg Fluralaner/kg BW once, or with 1 mg Fluralaner/kg BW in a repeated dose of 0.5 mg/kg BW on 2 occasions, 7 days apart.

On day 0 (and group D additionally on day 7), the hens in groups A-D received Fluralaner via medicated drinking water. Group E received un-medicated drinking water ad libitum.

The dose to be administered was calculated based on average body weights of each treatment group, measured one day before treatment (day −1, day 6). A concentrated Fluralaner solution was diluted in the drinking water to prepare medicated drinking water ready for consumption, via the following dosing regimen:

The volume of medicated water offered per group on day 0 (group D also on day 7) was approximately 50% of the calculated mean daily water intake measured previously in the respective group in order to ensure consumption of the full dose.

Once all medicated water was consumed the other 50% volume of the mean daily water intake was supplied as unmedicated tap water in the same drinker.

On days 1, 5, 8, 12, 15, 19 and 22, four of the six hens per group were infested with approximately 200 vital, *D. gallinae* mites (unfed nymphs and adults that had starved before infestation for 7 days).

From each infested hen approximately 25 engorged mites were collected after a few hours of presence in the animal box, next they were incubated for approximately 24 hours, after which their status was observed. The dead, damaged and/or live mites were counted visually using a binocular.

Mites were classified as dead if no movement was determined or mites lay in a dorsal position. Mites were classified as damaged if their movement was uncoordinated.

The Mite Mortality and Mite Inhibition percentage was calculated for each treated group in comparison to a non-treated negative control group.

1.2. Results

Fluralaner was well tolerated in the hens.

The % mortality and % inhibition of red mites assessed approximately 24 hours after the infestation of hens that received Fluralaner orally via drinking water are given in Tables 1 and 2. A fast onset of action was demonstrated for all administered doses.

TABLE 1

% mortality of *D. gallinae* assessed 24 hours after infestation

| Group | Fluralaner (mg/kg BW) | % Mortality of mites 24 hours after infestation on day | | | | | | |
|---|---|---|---|---|---|---|---|---|
| | | 1 | 5 | 8 | 12 | 15 | 19 | 22 |
| A | 2 | 100 | 100 | 100 | 100 | 77 | 1 | 0 |
| B | 1 | 100 | 100 | 100 | 94 | 77 | 2 | 0 |
| C | 0.5 | 100 | 100 | 97 | 55 | 15 | 0 | 0 |
| D | 1 (2 × 0.5) | 100 | 100 | 100 | 100 | 98 | 59 | 14 |

TABLE 2

% inhibition of *D. gallinae* assessed 24 hours after infestation

| Group | Fluralaner (mg/kg BW) | % Inhibition of mites 24 hours after infestation on day: | | | | | | |
|---|---|---|---|---|---|---|---|---|
| | | 1 | 5 | 8 | 12 | 15 | 19 | 22 |
| A | 2 | 100 | 100 | 100 | 100 | 81 | 14 | 0 |
| B | 1 | 100 | 100 | 100 | 95 | 81 | 3 | 0 |
| C | 0.5 | 100 | 100 | 100 | 75 | 19 | 0 | 0 |
| D | 1 (2 × 0.5) | 100 | 100 | 100 | 100 | 99 | 66 | 27 |

On each assessment time point, mites observed from the untreated control group were vital and showed their normal behaviour.

Example 2: Efficacy of Fluralaner in Medicated Drinking Water Against Northern Fowl Mite Infestation of Chickens As a further comparative example, studies comparable to those described in Example 1 were performed to demonstrate the high effectivity of isoxazoline in unsanitized medicated drinking water also against a natural infestation of layer chickens with Northern fowl mite (*O. sylviarum*). No vitamin E was present in the concentrated Fluralaner solution used to prepare the medicated drinking water.

The effectivity of an oral dosing regimen of Fluralaner was tested by administering medicated drinking water (via gavage) to laying hens, in 2 repeated doses of 0.25, 0.5 or 1.0 mg/kg body weight, administered 7 days apart, and challenging them with infestation by Northern fowl mites, via source birds and natural infestation. The birds were kept in separate pens, at 11 birds per pen.

The statistical analysis of results was based on mite count from each bird in the study, using pen as a random factor in the model, and mite counts were performed and recorded for individual birds.

Mite vent count reduction of the treated groups compared to the control group was the primary efficacy criterion. Effectiveness was demonstrated as there was a significant difference in *O. sylviarum* (p<0.05) mite vent counts between the Fluralaner treated- and the control groups.

Again Fluralaner was well tolerated in the hens, and provided significant efficacy against *O. sylviarum* when administered orally as 2 single doses of 0.25, 0.5, or 1 mg/kg BW, 7 days apart.

Early onset of action was observed in all doses, with statistically significant reductions in mite vent counts observed in all treated groups already beginning at day 1. The concentrations of Fluralaner in the birds' plasma increased proportionally to the dose administered.

An efficacy against Northern fowl mites (reduction in mite vent count) of 90% was demonstrated in all treated groups for at least 19 days, even despite the presence of untreated source birds in the same pen. Also, the source birds (5 per pen) maintained a natural mite infestation pressure throughout the study.

Duration of efficacy was dependent on the Fluralaner dose administered, and lasted for up to 19, 22 or 22 days after first treatment administration, for the 0.25, 0.5 or 1.0 mg/kg BW dose groups, respectively.

Example 3: Effect of Drinking Water Quality on Degradation of Isoxazoline

To assess what caused the degradation of Fluralaner in dilution in drinking water, the impact of different types and qualities of drinking water was tested. This was done by incubation of samples containing 1 μg/g of Fluralaner, in water that contained different ions at increased concentrations from average normal conditions. Samples were mixed and incubated for 7 days, either at 2-8° C., or at 40° C./75% relative humidity (RH). Fluralaner contents were measured before and after incubations.

3.1. Fluralaner Measurements

Isoxazolines such as Fluralaner can be detected and quantified by fast liquid chromatography methods, using standard equipment and procedures, such as UHPLC. Standard liquids for washing and as carrier are e.g.: LC grade Acetonitrile, Methanol, Formic acid, and MiliQ™ water can be prepared in house. Fluralaner is characterised based on its UV spectrum and retention profile, and quantified in reference to dilutions of standards.

3.2. Testing of Different Water Qualities

LoQ=Limit of Quantitation, the lowest concentration at which the analyte can reliably be detected. For Fluralaner by UHPLC the LoQ is 100 ng/ml.

TABLE 3

Different water qualities tested for effect on Fluralaner.

| Drinking water quality | Fluralaner content (μg/g) after 7 days at | |
|---|---|---|
| | 2-8° C. | 40° C./75% RH |
| Purified water | 0.90 | 0.92 |
| Water at pH = 4 | 1.23 | 1.26 |
| Water at pH = 10 | 0.78 | 0.79 |
| Soft water/low pH (1) | 0.88 | 0.89 |
| Hard water/high pH (2) | 0.92 | 0.96 |
| $Fe^{3+}$ water at 1 mg/l | 0.91 | 0.89 |
| $Na^+$ water at 300 mg/l | 0.85 | 0.84 |
| $K^+$ water at 300 mg/l | 0.90 | 0.80 |
| $Cu^{2+}$ water at 10 mg/l | 0.90 | 0.78 |
| $Al^{3+}$ water at 1 mg/l | 0.99 | 1.01 |
| $NO_3^-$ water at 100 mg/l | 0.92 | 0.93 |
| $PO_4^-$ water at 100 mg/l | 1.14 | 1.15 |
| $Cl^-$ water at 300 mg/l | 0.97 | 0.98 |
| $ClO^-$ water at 250 ppm | Not detected | Not detected |
| $ClO^-$ water at 150 ppm | <LOQ | <LOQ |
| $ClO^-$ water at 50 ppm | <LOQ | <LOQ |
| $ClO^-$ water at 5 ppm | <LOQ | <LOQ |
| $ClO^-$ water at 0.5 ppm | 0.99 | 0.82 |

(1) Soft water contained 30 mg $CaCl_2 \cdot 2H_2O$/l; pH was 6.2
(2) Hard water contained 500 mg $CaCl_2 \cdot 2H_2O$/l; pH was 8.1

Although these conditions of incubation applied were very demanding, it is evident from these results that especially hypochlorite is incompatible with an isoxazoline such as Fluralaner. Unfortunately hypochlorite concentrations over 0.5 ppm, up to 100 ppm and above may actually be used for water sanitizing purposes in animal farming operations. Because degradated isoxazoline cannot be active anymore as parasiticide, therefore this degradation needed to be prevented in some way, in order to allow mass application via the local drinking water used.

Of the effects detected, either positive of negative, only those of hypochlorite were found to be reproducible.

3.3. Analysis of Breakdown Products of Fluralaner

The breakdown products of Fluralaner by hypochlorite were analysed by LC-MS and UHPLC-MS. The aim was to determine molecular ion peaks of decomposition products in order to deduce their chemical identity.

Samples of medicated drinking waters from the incubations in different types of drinking water were analysed directly, but were found to be too dilute for mass detection.

To overcome this, direct incubations of samples of Fluralaner with hypochlorite were made: 1.5 mg/ml Fluralaner was dissolved in tetrahydrofurane containing water to dissolve the isoxazoline, and these were incubated with 5 ppm hypochlorite for 24 hours. These samples were tested by UHPLC-MS. For comparison, specific standards were also analysed of truncated Fluralaner molecules which could be potential breakdown products. By comparing the peaks of the hypochlorite incubated samples, to those of the standards, actual breakdown products could be identified.

Interestingly, two major breakdown products by hypochlorite of the original Fluralaner molecule were identified; each was cleaved at one of the amide groups that are in the side chain of the substituted benzamide moiety.

In tact Fluralaner molecule:

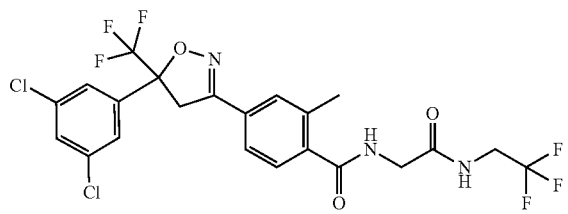 [SMILES: Cc1cc(C2=NOC(c3cc(Cl)cc(Cl)c3)(C(F)(F)F)C2)ccc1C(=O)NCC(=O)NCC(F)(F)F]

Hypochlorite breakdown products detected:

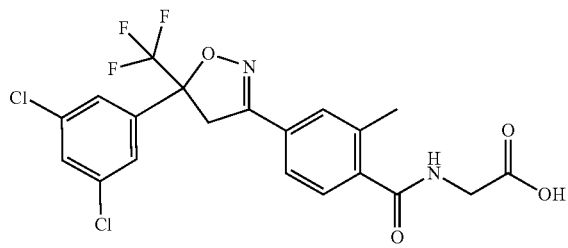 [SMILES: Cc1cc(C2=NOC(c3cc(Cl)cc(Cl)c3)(C(F)(F)F)C2)ccc1C(=O)NCC(=O)O]

2-[[4-[5-(3,5-dichlorophenyl)-5-(trifluoromethyl)-4H-isoxazol-3-yl]-2-methyl-benzoyl]amino]acetic acid, and

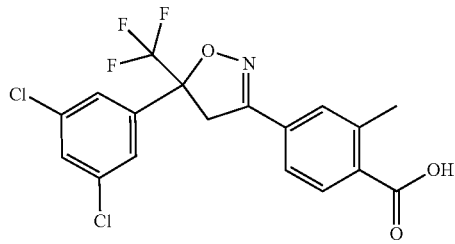 [SMILES: Cc1cc(C2=NOC(c3cc(Cl)cc(Cl)c3)(C(F)(F)F)C2)ccc1C(=O)O]

4-[5-(3,5-dichlorophenyl)-5-(trifluoromethyl)-4H-isoxazol-3-yl]-2-methyl-benzoic acid

Example 4: Prevention of Isoxazoline Degradation in Sanitized Medicated Drinking Water The inventors tested several ways to prevent the degradation of isoxazolines in drinking water of different qualities, especially in drinking water containing an oxidising sanitizer, such as hypochlorite.

4.1. Sample Preparation

To the base of a pharmaceutical composition as described herein, comprising isoxazoline, solvent, and surfactant, different compounds were added as protectors to prevent breakdown of isoxazoline when diluted in water with a water sanitizer such as hypochlorite.

The base composition was: 0.95% w/w Fluralaner in a mixture of Transcutol V and Tween 80 in 25:75 ratio, whereby the Transcutol and Tween are at a % w/w that was 99.05 minus the % w/w of the protector used. Where the protector amount was zero, this sample served as unprotected control sample. The Fluralaner level was determined using UHPLC. The alpha-tocopherol used was alpha-tocopherol EP (Fluka).

TABLE 4

Tested protectors and amounts:

| Protector | $M_w$ (g/mol) | Amount of protector in the pharmaceutical composition (in % w/w) |
|---|---|---|
| Lauryl gallate (dodecyl gallate) | 338.44 | 6.4 |
| BHA (butylated hydroxyanisole) | 180.25 | 3.4 |
| BHT (butylated hydroxytoluene) | 220.35 | 4.2 |
| α-Tocopherol (vitamin E) | 430.71 | 8.2 |
| Sodium metabisulfite | 190.10 | 3.6 |
| Sodium sulphite (anhydrous pure) | 126.04 | 2.4 |
| EDTA (acid pure) | 292.24 | 5.5 |

To prepare the test samples, the required amounts of Transcutol and Tween were measured, combined in a beaker at room temperature, and mixed magnetically. Next, when no protector was added, the required amount of Fluralaner was weighed, added, and mixed until complete dissolution, which usually required about 10 minutes, at 70% speed. The prepared concentrated solution of Fluralaner at 0.95% w/w, had a clear and yellow appearance. The complete dissolution was verified visually. Next the density of the resulting solution was checked with a Densimeter, at 20° C.

For samples containing a protector, Fluralaner was added to a mixture of Transcutol V, Tween 80 and protector, and then mixed to dissolve.

BHT, BHA and lauryl gallate, which are solids, were dissolved in the base composition, which took up to 60 minutes; the alpha-tocopherol, which is a viscous liquid started to mix quickly but required up to 30 minutes for mixing to be complete.

4.2. Test of Prevention of Degradation by Oxidizing Sanitizer

To test the capacity of the different protectors to prevent degradation of Fluralaner in medicated drinking water by an oxidising sanitizer, samples of the pharmaceutical composition as prepared above were diluted to different concentrations, and incubated with different amounts of hypochlorite. Concentrations of Fluralaner in medicated drinking water used were: 1, 5, and 10 μg/ml. One negative control sample was also included, which did not contain Fluralaner.

The hypochlorite used was from a 13% sodium hypochlorite solution (Acros Organics), which was prepared into samples with a concentration of hypochlorite of: 0, 0.5, 2, 5, or 10 ppm, wherein 1 ppm equals 20 μM. Samples without hypochlorite served as positive controls. While the dilutions of hypochlorite were made in purified water, one additional sample at 5 ppm hypochlorite was prepared in standard tap water (Angers, France). Control samples were tested at day zero, all others were tested after an incubation for 7 days at 40° C./75% RH.

The concentration of protector in the test sample was dependent of the dilution factor of the concentrated Fluralaner composition applied: 1:10,000, 1:2000, or 1:1000, respectively.

4.3. Results of Prevention of Degradation by Oxidizing Sanitizer

The compounds Na-metabisulfite, Na-sulphite, and EDTA were not soluble in the base pharmaceutical composition, therefore they could not be used as protector added to the concentrated solution. The compound Lauryl gallate was soluble, however this presented an orange coloration after mixing. As this was suspected to represent some type of interaction or degradation, this compound was not tested further. The compounds BHA and BHT were soluble, and did not show an immediate colour-change, but a colour change did develop a few days into the incubation in sanitized water. Therefore only alpha-tocopherol was suitable as protector.

TABLE 5

Effect of incubation in sanitized medicated drinking water on Fluralaner content; no protector

| Conc. Fluralaner | Hypochlorite concentration in medicated drinking water (ppm) | | | | | | |
|---|---|---|---|---|---|---|---|
| (µg/ml); no protector | 0 T = 0 | 0 | 0.5 | 2 | 5 | 5 (tapw.) | 10 |
| | | T = 7 d at 40° C./75% RH | | | | | |
| 0 | — | — | — | — | — | — | n.d. |
| 1 | 0.93 | 0.92 | 0.91 | 0.91 | 0.29 | 0.13 | <LoQ |
| 5 | 5.50 | 5.51 | 5.52 | 5.50 | 5.31 | 4.43 | 1.54 |
| 10 | 10.10 | 10.07 | 10.03 | 10.03 | 9.97 | 8.69 | 5.05 |

— = not done
n.d. = not detectable
LoQ = 50 ng/ml

TABLE 6

Effect of incubation in sanitized medicated drinking water on Fluralaner content; alpha-tocopherol as protector

| Conc. Fluralaner | Hypochlorite concentration in medicated drinking water (ppm) | | | | | | |
|---|---|---|---|---|---|---|---|
| (µg/ml); with α-tocopherol | 0 T = 0 | 0 | 0.5 | 2 | 5 | 5 (tapw.) | 10 |
| | | T = 7 d at 40° C./75% RH | | | | | |
| 0 | — | — | — | — | — | — | n.d. |
| 1 | 0.91 | 0.89 | 0.91 | 0.92 | 0.89 | 0.86 | 0.05 |
| 5 | 5.52 | 5.45 | 5.52 | 5.52 | 5.49 | 5.42 | 5.56 |
| 10 | 10.14 | 10.01 | 10.10 | 10.10 | 9.99 | 9.94 | 10.05 |

From these results it was apparent that without any protector, Fluralaner becomes degradated in sanitized drinking water: after 7 days at 40° C., in 5 or 10 ppm hypochlorite, this significantly degradated the Fluralaner, especially when tested in tap water.

However, as is evident from Table 6, alpha-tocopherol could completely protect Fluralaner at 5 or 10 µg/ml from degradation in sanitized drinking water, even up to 7 days, even when at 40° C., and even with up to 10 ppm hypochlorite. Only for the lowest concentration Fluralaner and the highest concentration hypochlorite tested (1 µg/ml and 10 ppm), the alpha tocopherol could not protect. However this is not a problem, because in practice medicated water will not be used after 7 days, but rather within 1 day. Also, the concentration of Fluralaner in the sanitized medicated drinking water will usually be higher, namely above 5, 10, or even 15 µg/ml.

Again, the concentration of vitamin E used depended on the dilution factor of the concentrated Fluralaner composition applied.

Example 5: Variation of Concentration of Vitamin E

In a follow-up experiment, it was demonstrated that vitamin E, even at a reduced concentration can still effectively protect against degradation of isoxazoline by an oxidising sanitizer. While in Example 4.3 alpha-tocopherol was used in the pharmaceutical composition at 8.2% w/w, it was now tested at 80% of that value, namely at 6.6% w/w.

Pharmaceutical compositions according to the invention were prepared, containing either 8.2 or 6.6% w/w alpha-tocopherol. Also one base composition was prepared without protector. These were diluted 1:10.000 to prepare medicated drinking waters with 1 µg/ml Fluralaner. Next hypochlorite was added to 5 ppm, and 20 ml samples were filled-out in 50 ml glass vials, sealed with a rubber stopper, and stored for 7 days at 40° C./75% RH.

The amount of Fluralaner of the three samples was measured at t=0 and at t=7 days using UHPLC. The concentration of the vitamin E in the final test sample was 1:10,000 of 6.6 or 8.2% w/w.

TABLE 7

Effect of reduced amount of vitamin E

| Vitamin E conc. (% w/w in pharm. comp.) used at 1:10.000 | Fluralaner conc. (µg/ml) after incubation in 5 ppm ClO— at 40° C./75% RH, for | | Reduction t = 0 to t = 7 in % |
|---|---|---|---|
| | t = 0 d | t = 7 d | |
| 0 | 0.80 | 0.15 | 81 |
| 6.6 | 0.91 | 0.49 | 46 |
| 8.2 | 0.90 | 0.49 | 46 |

As can be seen from Table 7, the Fluralaner in dilutions without alpha-tocopherol was considerably degradated by 5 ppm hypochlorite after 7 days at 40° C.: the reduction in Fluralaner amount was 81%.

However, with alpha-tocopherol this reduction was almost halved, from 81% to 46%. Interestingly, this level of protection was obtained with sample prepared from pharmaceutical composition comprising 8.2% w/w vitamin E, but also with the sample from pharmaceutical composition comprising 6.6% w/w vitamin E. This indicates that both these amounts of vitamin E in a pharmaceutical composition according to the invention can provide an equally effective protection to Fluralaner when diluted in drinking water comprising an oxidizing sanitizer.

Example 6: Stability of Pharmaceutical Composition Comprising a Protector

Similar to the experiments described in Example 3 above, where the effect of water quality on Fluralaner-containing medicated drinking water was tested; here samples of the pharmaceutical composition were tested for an effect of the addition of a protector, on their stability during prolonged storage.

6.1. Accelerated Stability Testing of Pharmaceutical Composition

To test the long term stability of the pharmaceutical composition with a protector, some samples were stored under conditions of accelerated ageing. Samples of the pharmaceutical composition with or without one of the protectors, were filled out in portions of 7 gram each, in 10 ml glass vials, sealed with rubber stoppers, and stored under different conditions: 2-8° C.; 30° C./65% RH; 40° C./75% RH, and 50° C. Samples were taken for analysis at t=0, 1, 2, 4, and 8 months; the Fluralaner level was determined using UHPLC; the decrease over time, as compared to the t=0 samples was investigated.

6.2. Results of Accelerated Stability Testing of the Pharmaceutical Composition

Placebo: No change was detected.

Lauryl gallate: Shortly after preparation of the pharmaceutical composition, an orange coloration appeared, similar to what was apparent in sanitized medicated drinking water, described in Example 4. As this indicated some type of interaction or degradation, this protector was not used further.

BHT and BHA: Stability results up to 4 months were obtained, when the tests were terminated because of the detection of a discoloration, similar to what was apparent in sanitized medicated drinking water tests. This is not acceptable for the commercial product, therefore these were not used further.

Alpha-tocopherol: Stability was tested up to 8 months: no significant reduction of the level of Fluralaner, or of the level of alpha-tocopherol was observed, under any of the storage conditions. Currently stability data up to 18 months are available, and these show the same positive results of a lack of interaction by alpha-tocopherol in the pharmaceutical composition according to the invention.

Example 7: Examples of Dosing Calculations for Preparation of Medicated Drinking Water Some examples are provided for the calculation of ways to prepare a medicated drinking water according to the invention, for administration to e.g. a group of laying hen chickens, either by way of a dosing pump, or by way of a medication tank.

7.1. Use of a Dosing Pump:
Exemplary Starting Values:
Number of chickens to be treated: 3500 (when not known exactly, best guess the number)
Average weight per hen: 1.7 kg (measured shortly before administration, on a number of animals that allows a significant measurement)
Concentration of Fluralaner in pharmaceutical composition: 10 mg/ml
Total Fluralaner dose to be administered this treatment period: 0.5 mg/kg BW
Average water consumption over 4 hr treatment period: 200 litres (measured shortly before treatment)
Dosing pump injection rate: 5%
Concentration of vitamin E in pharmaceutical composition: 8.2% w/w
Calculated Values:
Total BW to be treated: 3500×1.7 kg=5950 kg
Total amount of Fluralaner required: 5950 kg×0.5 mg/kg=2975 mg
Total amount of pharmaceutical composition required for making the dilution: 2975 mg: 10 mg/ml=297.5 ml
Volume of stock solution required for dosing pump: 5% of 200 l=10 litres
Preparation of 10 l dosing pump stock solution: 9.7025 l water+297.5 ml pharmaceutical composition (mix adequately)
Concentration of Fluralaner in stock solution for dosing pump: 2975 mg in 10 l=297.5 mg/l
Concentration of Fluralaner in final medicated drinking water: 2975 mg in 200 l=14.88 mg/l
Dilution factor of pharmaceutical composition in final medicated drinking water: 297.5 ml in 200 l=1:672
Amount of vitamin E in final medicated drinking water: 1:672 of 8.2% w/w=0.0122% w/w=122 µg/g 7.2. Use of a Medication Tank
Exemplary Starting Values:
Number of chickens to be treated: 3500 (when not known exactly, best guess the number)
Average weight per hen: 1.7 kg (measured shortly before administration, on a number of animals that allows a significant measurement)
Concentration of Fluralaner in pharmaceutical composition: 10 mg/ml
Total Fluralaner dose to be administered this treatment period: 0.5 mg/kg BW
Average water consumption over 4 hr treatment period: 200 litres (measured shortly before treatment)
Concentration of vitamin E in pharmaceutical composition: 8.2% w/w
Medication tank volume to be used: 175 litres
Calculated Values:
Total BW to be treated: 3500×1.7 kg=5950 kg
Total amount of Fluralaner required: 5950 kg×0.5 mg/kg=2975 mg
Total amount of pharmaceutical composition required for making the dilution: 2975 mg: 10 mg/ml=297.5 ml
Preparation of medication tank water: 174.7 l water with 297.5 ml of pharmaceutical composition (mix adequately)
Concentration of Fluralaner in medication tank water: 2975 mg in 175 l=17 mg/l
Concentration of Fluralaner in final medicated drinking water: same as medication tank water
Dilution factor of pharmaceutical composition in final medicated drinking water: 297.5 ml in 175 l=1:588
Amount of vitamin E in final medicated drinking water: 1:588 of 8.2% w/w=0.0139% w/w=139 µg/g

The invention claimed is:

1. A Method for the treatment or prevention of parasite infestation of animals, comprising the administration to the animals of the medicated drinking water during a treatment period
wherein the medicated drink water comprises
a) previously sanitized animal drinking water and
b) a pharmaceutical composition comprising an isoxazoline in a pharmaceutically acceptable solvent and a co-solvent, and alpha tocopherol, wherein the isoxazoline is the compound fluralaner;
wherein the pharmaceutical composition comprises at least 6% of the alpha tocopherol and the previously sanitized animal drinking water comprises between 3 ppm and 10 ppm of residual chlorine; and
wherein the fluralaner is stable in the medicated drinking water and wherein the treatment period is between 1 and 24 hours.

2. A Method for controlling and/or reducing parasitic arthropods in animal surroundings, the method comprising the administration to the animals of the medicated drinking water during a treatment period
wherein the medicated drink water comprises
a) previously sanitized animal drinking water and
b) a pharmaceutical composition comprising an isoxazoline in a pharmaceutically acceptable solvent and a co-solvent, and alpha tocopherol, wherein the isoxazoline is the compound fluralaner;
wherein the pharmaceutical composition comprises at least 6% of the alpha tocopherol and the previously sanitized animal drinking water comprises between 3 ppm and 10 ppm of residual chlorine; and
wherein the fluralaner is stable in the medicated drinking water and wherein the treatment period is between 1 and 24 hours.

* * * * *